(12) United States Patent
Olson

(10) Patent No.: US 8,151,369 B2
(45) Date of Patent: *Apr. 10, 2012

(54) PROTECTIVE DEVICE

(76) Inventor: Keith D. Olson, Elk Grove Village, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,712

(22) Filed: Mar. 22, 2011

(65) Prior Publication Data

US 2011/0167546 A1  Jul. 14, 2011

Related U.S. Application Data

(63) Continuation of application No. 11/263,104, filed on Oct. 31, 2005, now Pat. No. 7,941,867.

(60) Provisional application No. 60/629,574, filed on Nov. 19, 2004.

(51) Int. Cl.
   *A41D 13/00* (2006.01)

(52) U.S. Cl. ............................................................ 2/22

(58) Field of Classification Search .................. 2/22, 24, 2/455, 911; 128/881, 882, 878; 602/23, 602/26, 62

See application file for complete search history.

(56) References Cited

U.S. PATENT DOCUMENTS

| | | | |
|---|---|---|---|
| 3,945,042 A | 3/1976 | Lobo | |
| 4,042,975 A | 8/1977 | Elliott, Jr. et al. | |
| 4,325,148 A | 4/1982 | Livernois | |
| 5,007,111 A | 4/1991 | Adams | |
| 5,337,417 A | 8/1994 | Whiteside et al. | |
| 5,545,128 A | 8/1996 | Hayes et al. | |
| 5,652,956 A | 8/1997 | Hoshizaki et al. | |
| 5,768,717 A | 6/1998 | LeSueur | |
| 2002/0184693 A1 | 12/2002 | Beland | |

FOREIGN PATENT DOCUMENTS

| | | |
|---|---|---|
| GB | 1 549 230 | 7/1979 |
| GB | 2 171 893 A | 9/1986 |
| GB | 2 285 910 A | 8/1995 |
| GB | 2 328 859 A | 3/1999 |
| WO | WO 96/19124 | 6/1996 |
| WO | WO 00/53275 | 9/2000 |
| WO | WO 01/87432 A2 | 11/2001 |
| WO | WO 01/87432 A3 | 11/2001 |

OTHER PUBLICATIONS

Japanese Office Action dated Oct. 18, 2010, 6 pages.

*Primary Examiner* — Tejash Patel

(74) *Attorney, Agent, or Firm* — Brinks Hofer Gilson & Lione

(57) ABSTRACT

An energy absorbing device suitable for wearing by humans, or for use in a prosthetic device or robot is provided. The device including support structures which may conform to the contours of limbs, and have the capability of being removeably attached to the limbs. Plates are attached, either fixedly or slideably, to the support structures and adjacent ends of plates may be joined with a flexible link. As the limbs flex at a joint, the slideably attached plate slides to accommodate the rotational motion between the limbs at the joint.

14 Claims, 20 Drawing Sheets

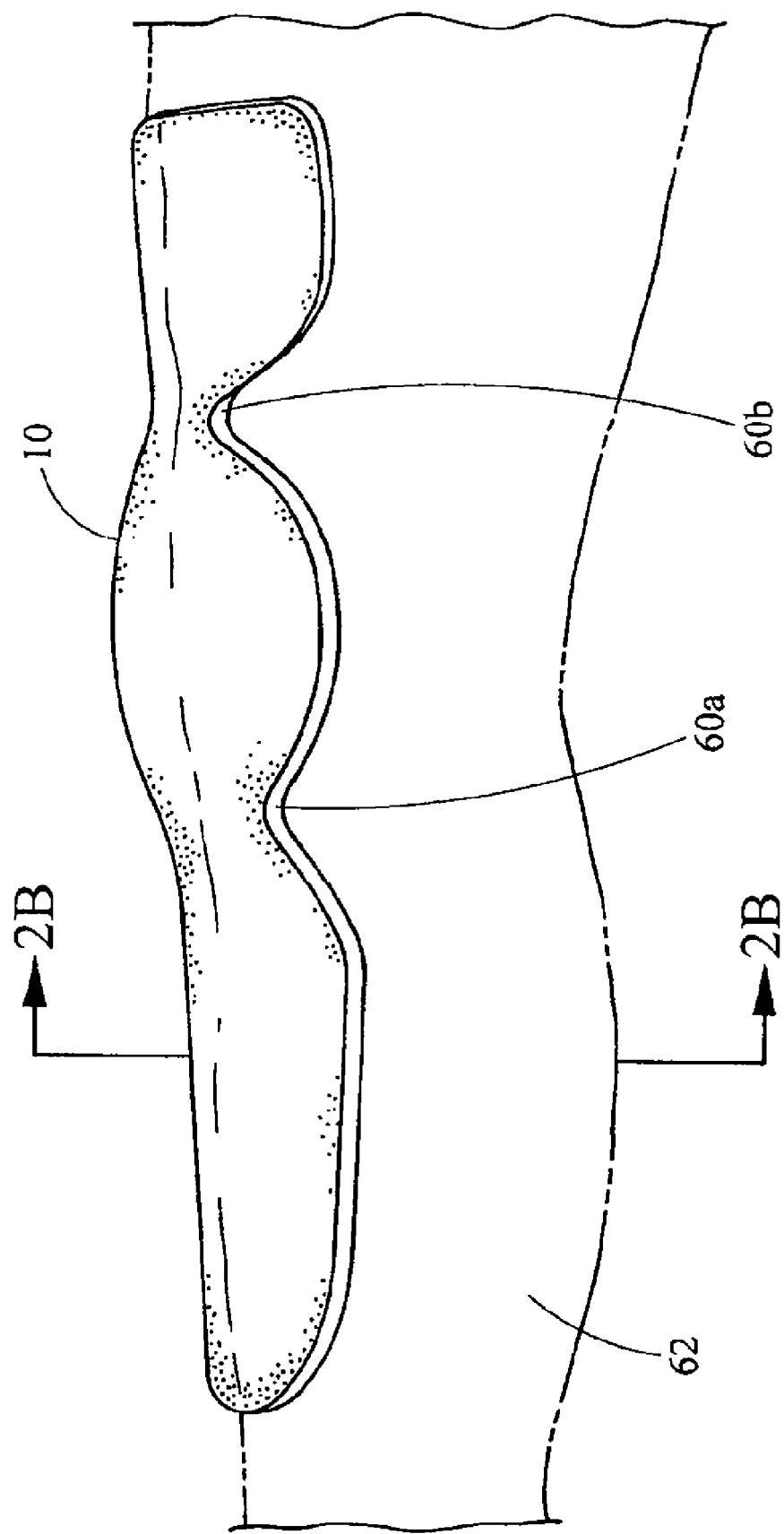

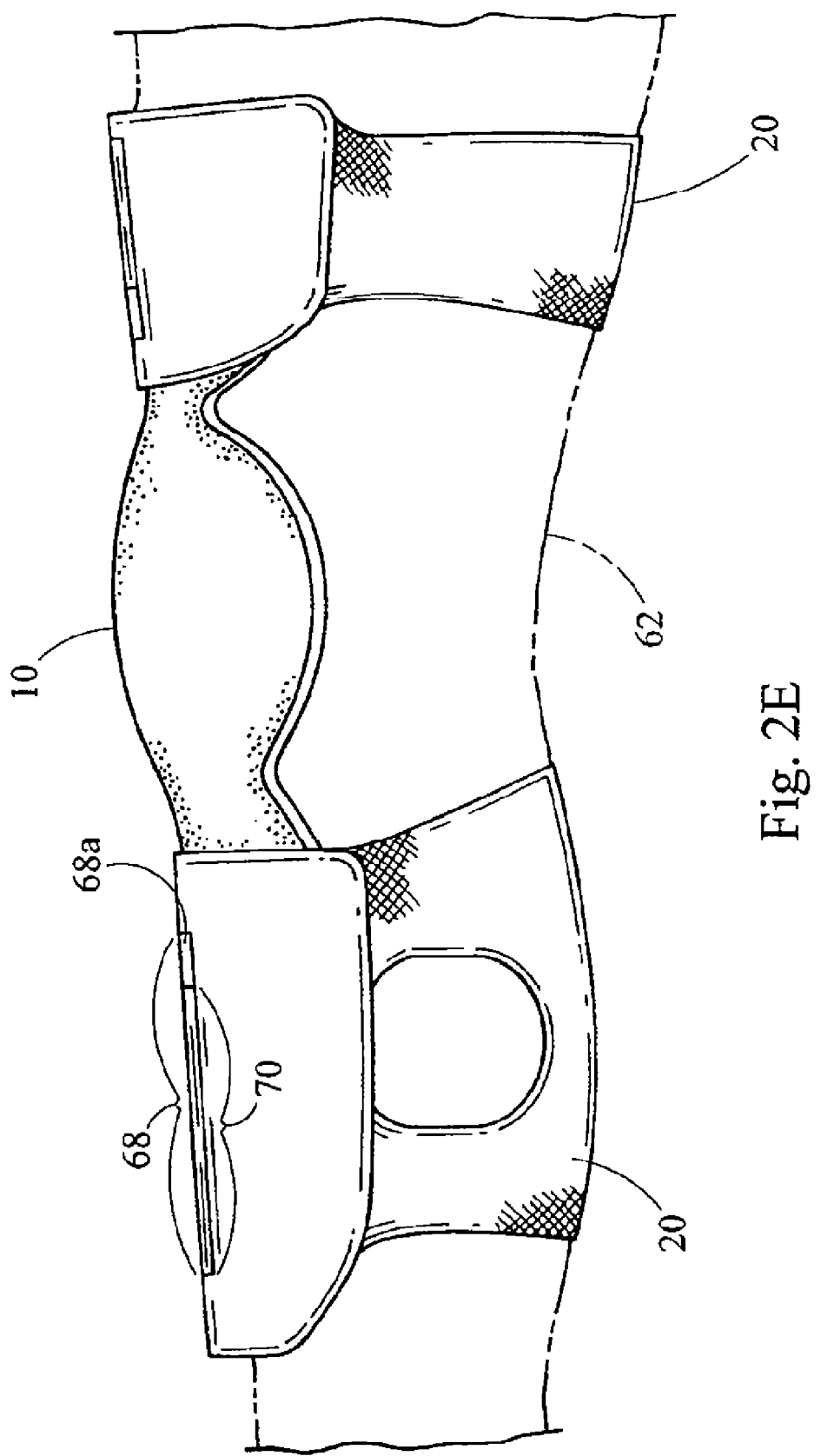

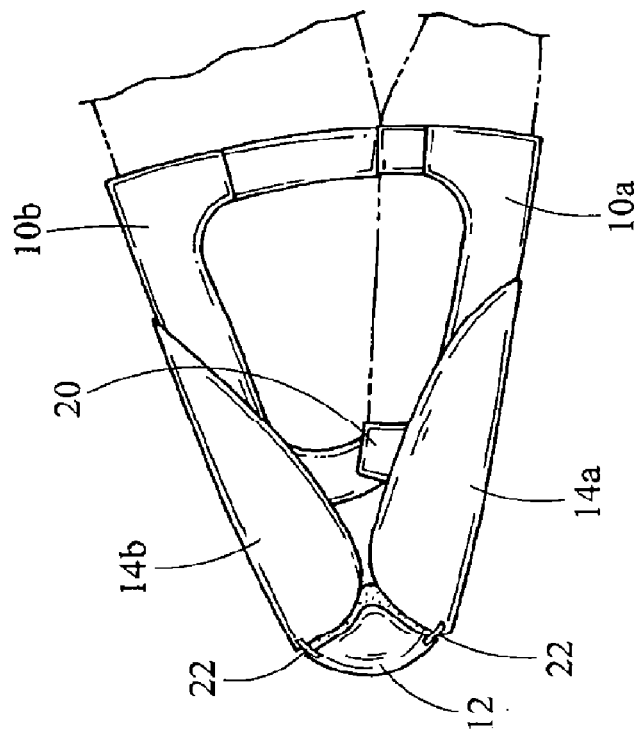
Fig. 9C
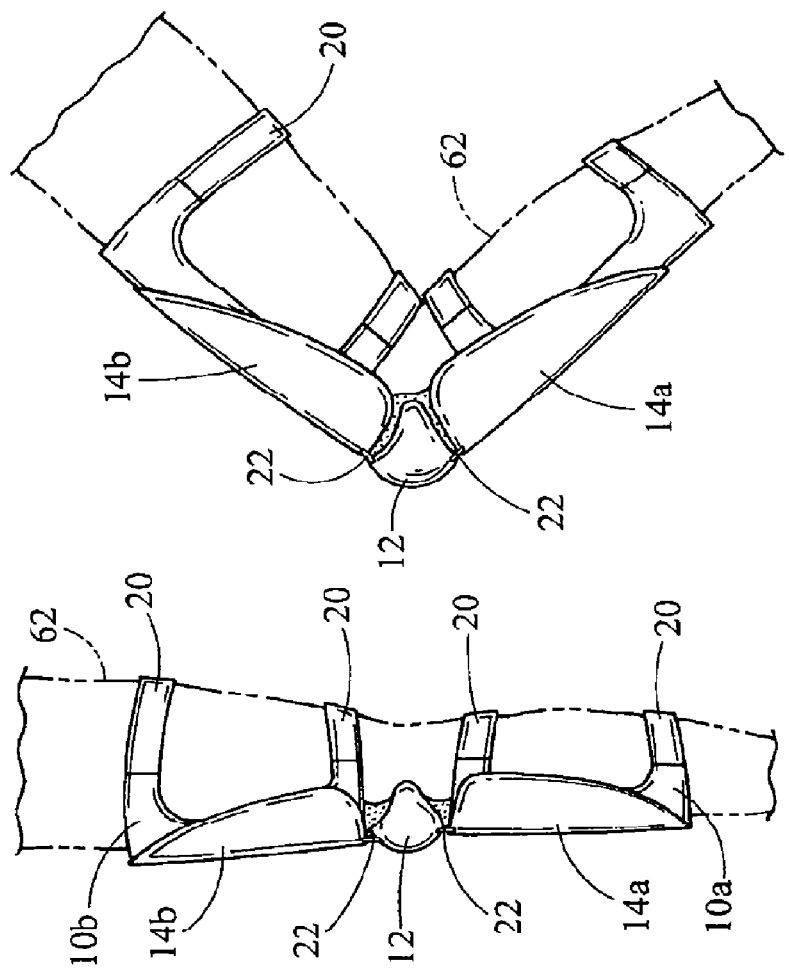
Fig. 9B
Fig. 9A

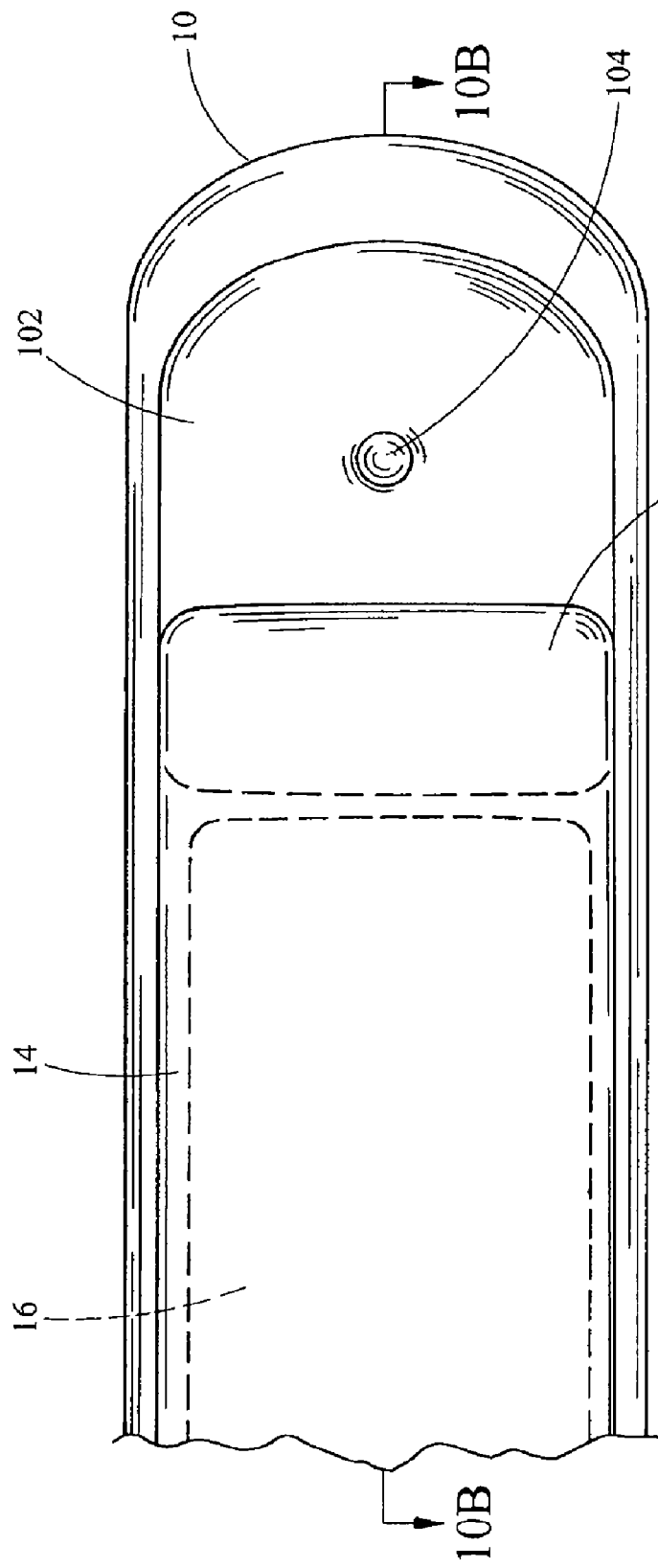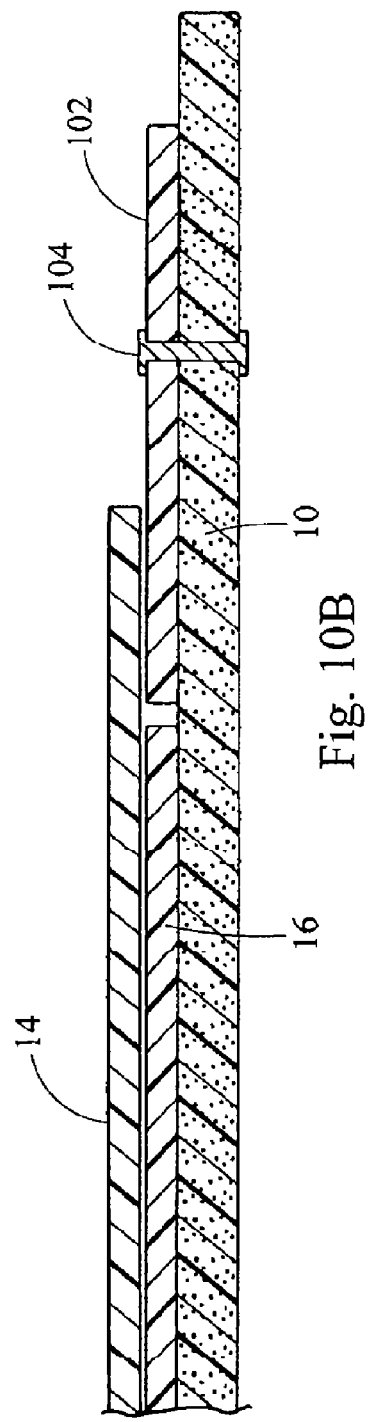
Fig. 10A
Fig. 10B

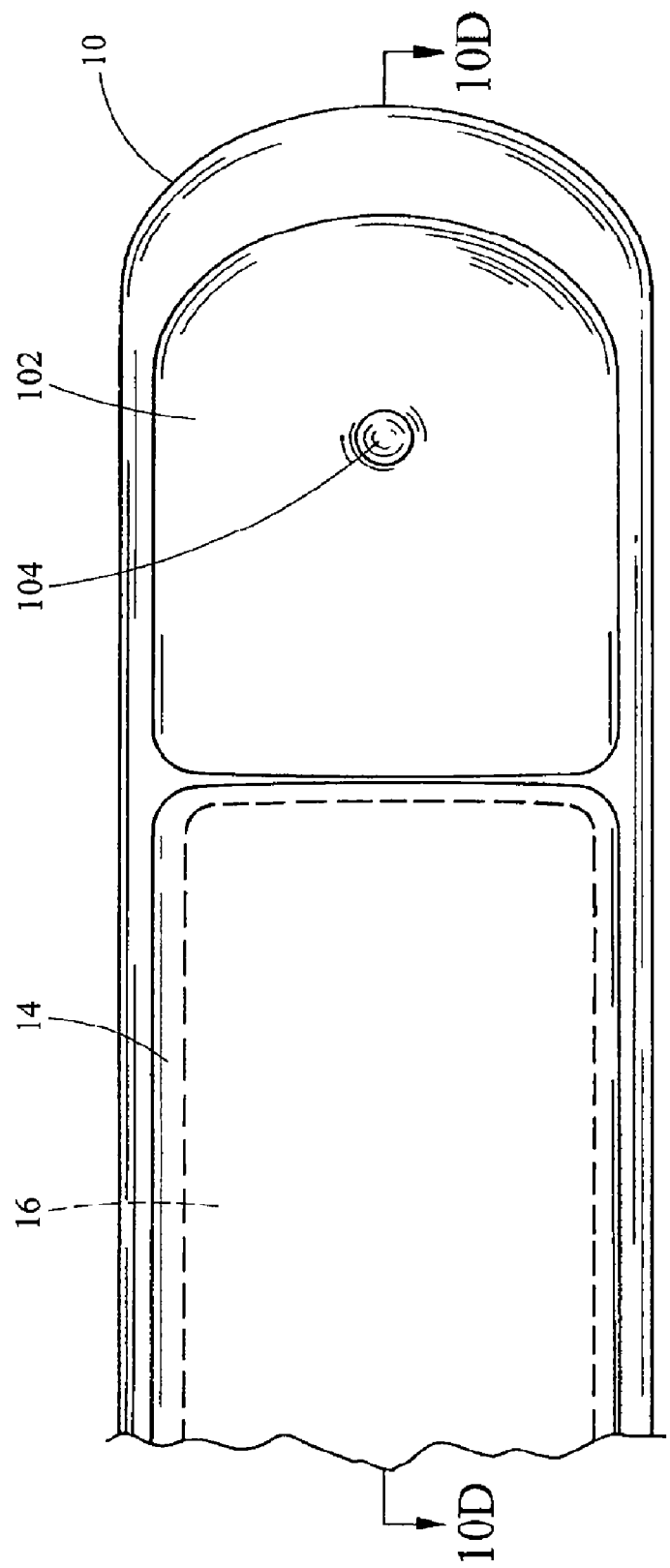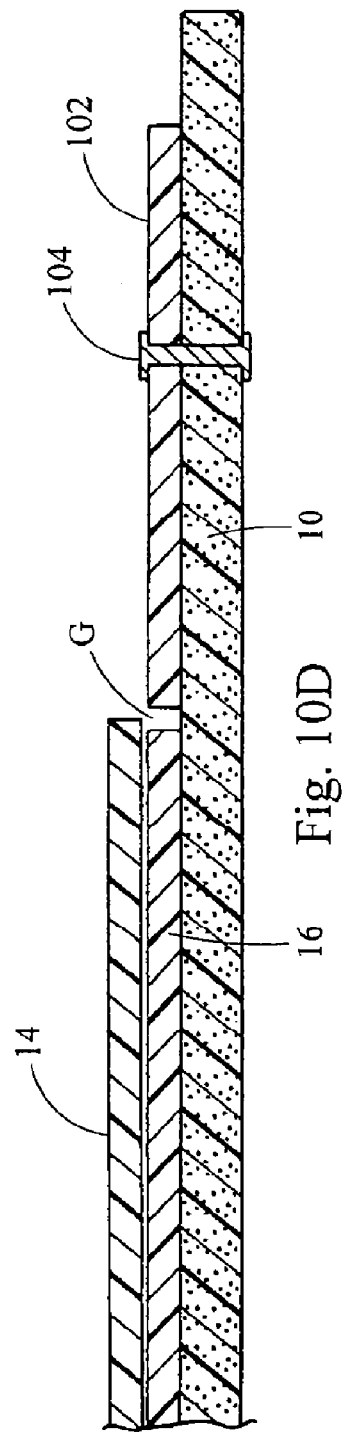
Fig. 10C
Fig. 10D

PROTECTIVE DEVICE

This application is a continuation of U.S. application Ser. No. 11/263,104, filed on Oct. 31, 2005 now U.S. Pat. No. 7,941,867 which claims the benefit of priority to U.S. provisional application No. 60/629,574, which was filed on Nov. 19, 2004.

TECHNICAL FIELD

This application relates to providing protection to the human body or an apparatus from external forces, and in particular with respect to articulated portions thereof.

BACKGROUND

In sports, in performing manual labor, and in military operations, injuries to both soft tissue and bone may occur due to impact forces. Other injuries may result form repetitive pressure on a body part, such as occurs when kneeling. Systems for providing plates to absorb or spread such forces are known and are used. However, while affording such protection, they are uncomfortable to wear, often shift location with repeated flexing, may require additional exertion to bend, and may limit the range of motion to less that of which a human can reasonably perform without injury.

SUMMARY

A wearable protective device is disclosed which permits articulated movement with minimal additional muscular effort. The device includes one or more sleeves adapted so as to be fitted to a body part, such as a leg, arm or torso. A first plate is fixedly attached to the sleeve, and a second plate is adapted to be slideably attached to the sleeve. The first plate and the second plate may communicate with each other by a hinge or link so that the distance between the first plate and the second plate is substantially fixed, while the angle between the principal planes of the first plate and the second plate may be variable. The sleeve may be comprised of one or more segments, which may be formed integrally with each other, or as separated pieces.

Plates not slideably attached to the sleeve may be permanently attached to a sleeve by riveting, by adhesives, by sewing, or other similar process. In another aspect, plates may be non-permanently attached to the sleeves by using VELCRO, DUALLOCK, or similar materials.

The slideably attached second plate may be mounted such that the second plate has an engaging shape on a side facing the sleeve, which mates with a captivating shape in a plate slide member such that the slideable plate may slide substantially linearly in a direction parallel to the surface of the sleeve and along the body part. The plate slide member may be either permanently or non-permanently mounted to the sleeve, by methods as described above. In addition, the slide plate member may be formed such that it is part of the sleeve or captivated by the sleeve. The positions of the captivating member and the engaging shape may be interchanged.

The link connecting the first and second plates may be a strap, ligature, hinge or other means of connecting adjacent ends of the first and second plates which permits the first and second plates to rotate angularly with respect to each other about an axis, the axis being approximately parallel to the intersection of planes passing through the first and second plates, such that the relative motion of the first and second plates approximates that of a hinge. Herein, the term "hinge" is used to represent the link or other flexible connection between adjacent ends of plates. The link may be able to push or pull the plates apart, approximately maintaining the distance of the gap and may be flexible enough to bend through a range bending angles.

Plates having a slideable mounting arrangement to a plate slide member will be referred to as "slideable" plates, and plates whose mounting is not slideable will be referred to as "fixed" plates. "Fixed" is distinguished from the terms "permanent" and "non-permanent" mounting as used herein, the latter terms referring to the ability to attach and detach a plate from the sleeve or the plate slide member from the sleeve or a plate slide member or another plate, regardless of whether the plate be slideable or fixed with respect to motion.

There may be more than one fixed plate, and more than one slideable plate, and more than one of each type of plate may be mounted to a sleeve. The sleeves may be either substantially in the form of a cylinder such that the device may be slid onto body or limb, or the side or a portion of the side approximately opposite to the plates may be omitted and a strap or other means provided for fastening the device to the user. Alternatively, the sleeve may be incorporated into, or attached to, clothing or a suspender belt so as to transfer some of the apparatus weight to the body. The sleeves may be secured to the limb by having elastic properties, by straps having self-adhering properties, by buckles, or the like.

Each plate for the fixed and slideable plates, and plate slide member, may be shaped and formed and dimensioned such that it conforms approximately to the shape of the body part to which it is applied by the sleeve and attachment arrangement.

In another aspect, the attachment of the plates to the plate slide member, or to the sleeve may be configured such that the application of sufficient force in a direction other than substantially orthogonal to the plate surface may cause the plate to detach from the sleeve or the plate slide member, or the plate slide member to detach from the sleeve.

A fixed plate may be disposed between two slideable plates, such that each of the slideable plates may slide and rotate with respect to the fixed plate when a body part joint is flexed, the fixed plate remaining in a substantially fixed position with respect to a kneecap or an elbow. Each slideable plate may be joined to the adjacent fixed plate with a hinge.

The plates may be formed of an impact resistant material, may be covered in whole or in part by a flexible or resilient material, and may contain a core of energy absorbing material.

The sleeve may be a composite or layered structure, including a stretch or high strength material or fabric, and may include a foam or other impact absorbing structure, including a gel, memory foam, energy resistant laminate and the like, disposed between the fixed plate, the slideable plate, or the plate slide member and the user. The sleeve may be constructed so that some of the areas have differing energy absorbing and stretching and flexing properties depending on the specific use. One or more straps, buckles or other fastening part is attached to, or formed integrally with, the sleeve and disposed so that the strap, buckle or other fastening part may be used to secure the sleeve to the limb or other body part. The sleeve may also be attached to an article of clothing.

Although the description herein may use the words body, limb, user and the like, which are terms normally relating to a human, the device may be equally used by other primates, horses or other animals, in robotic devices, and in prosthetic devices.

BRIEF DESCRIPTION OF THE DRAWINGS

FIG. 2A illustrates a side view of a sleeve conformable to a limb;

FIG. 2E illustrates a side view of an example of a protrusion from the slideable plate (not shown) engaged in the captivating groove for the state where the limb is substantially straight, and attachment straps for applying the apparatus to the limb;

FIG. 9A illustrates a side view of the apparatus attached to a limb, where the limb is in a straight state;

FIG. 9B illustrates the arrangement of FIG. 9A, where the limb is in a partially bent state;

FIG. 9C illustrates the arrangement of FIG. 9A, where the limb is in a substantially fully bent state;

FIG. 10A illustrates a detail of a slideable plate portion of the apparatus, where an auxiliary plate is disposed so as to maintain the coverage of a sleeve portion, shown when the limb is in a substantially straight state and the slideable plate and the auxiliary plate overlap;

FIG. 10B is a cross-section view along line B-B of the arrangement of FIG. 10A.

FIG. 10C illustrates the assembly of FIG. 10A where the limb is in a substantially fully bent state, and the slideable plate and the auxiliary plate have moved with respect to each other;

FIG. 10D is a cross-section view along line D-D of the arrangement of FIG. 10C.

DETAILED DESCRIPTION

Exemplary embodiments may be better understood with reference to the drawings, but these embodiments are not intended to be of a limiting nature. Like numbered elements in the same or different drawings perform equivalent functions. When a specific feature, structure, or characteristic is described in connection with an embodiment, it will be understood that one skilled in the art may effect such feature, structure, or characteristic in connection with other embodiments, whether or not explicitly stated herein.

Figure 1A:
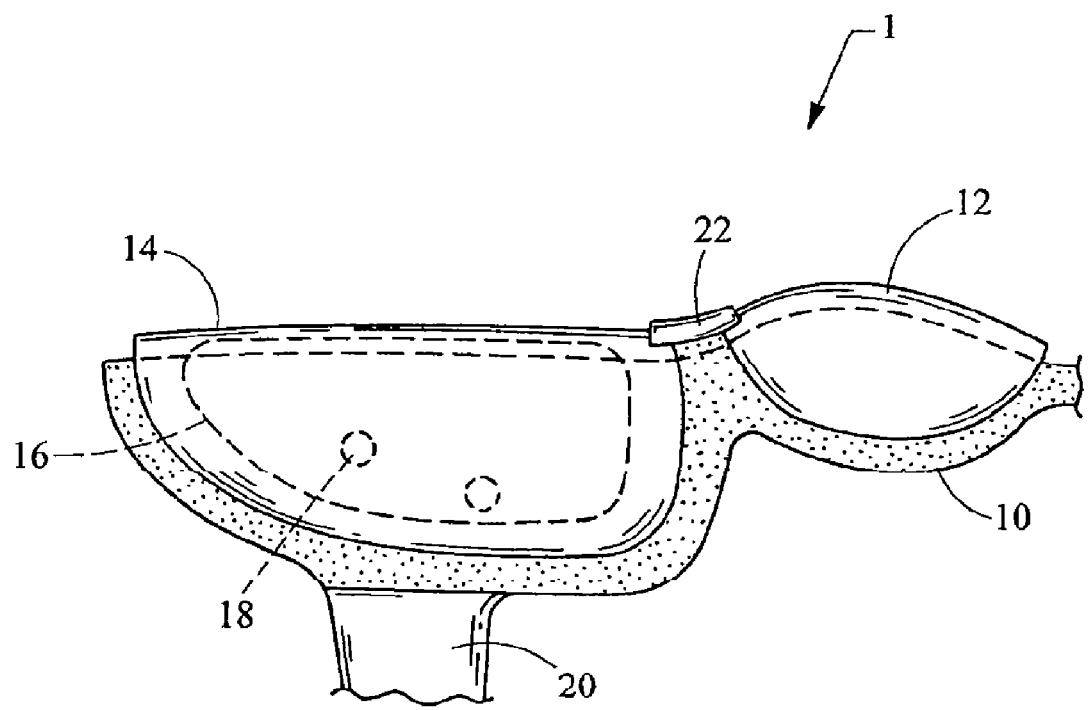
FIG. 1A illustrates a side view of a fixed plate and a slideable plate with a limb in a substantially straight state, where the plate slide member is permanently attached to the sleeve.

In a first example, illustrated in FIG. 1A, a side view of the apparatus illustrates the arrangement of plates (fixed 12, and slideable 14), a plate slide member 16, a sleeve 10, a hinge 22 and a portion of a strap 20, where the limb to which the apparatus is to be attached is in a straightened state. The limb may be a leg, an ankle, or an arm, with the fixed member 12 positioned over the flexing portion of the joint. Another slideable plate 14 may be positioned on the end of the fixed plate 12 opposite to the first sliding plate 14.

Sleeve 10 is shown as underlying the plate slide member 16 and the fixed plate 12, and the slideable plate 14 positioned over the plate slide member 16. The fixed plate 12 may be dimensioned and shaped such that it conforms to a body part such as a kneecap or elbow to be protected, and remains substantially in position with respect to the kneecap or elbow when a limb is flexed. The slideable plate 14 is dimensioned and shaped such that it conforms to a body part such as a long bone, shin or other body part to be protected, and may be adapted to be slideably attached to a plate slide member 16. Similarly, the plate slide member 16 may be dimensioned and shaped to conform to the same body part as the slideable plate 14, and adapted to slideably receive the corresponding slideable plate 14. The plate slide member 16 is permanently or temporarily attached to the sleeve 10. Similarly, the fixed plate 12 is permanently or temporarily attached to the sleeve 10. As shown, the plate slide member 16 is fixed to the sleeve 10 by rivets 18; however other attachment means, which may be either temporary or permanent, may be used, such as VELCRO or adhesive. Alternatively, the fixed plate 12 or the plate slide member 16 may be attached to the sleeve by providing an aperture or a pocket in the surface of the sleeve such that a portion of the fixed plate 12 or plate slide member 16 may be inserted therein. The fixed plate 12 or the plate slide member may be retained by the methods previously described, or by the elasticity of the outer surface material of the sleeve 10, or by sewing or the like.

The fixed 12 and slideable 14 plates are joined by a hinge 22, such that adjacent ends of the fixed 12 and slideable 14 plates are connected so that they may flex in a hinge-like manner. More than one slideable plate 14 may be connected to a single fixed plate 12, and slideable plates may be hingeably connected to slideable plates.

Figure 1B:
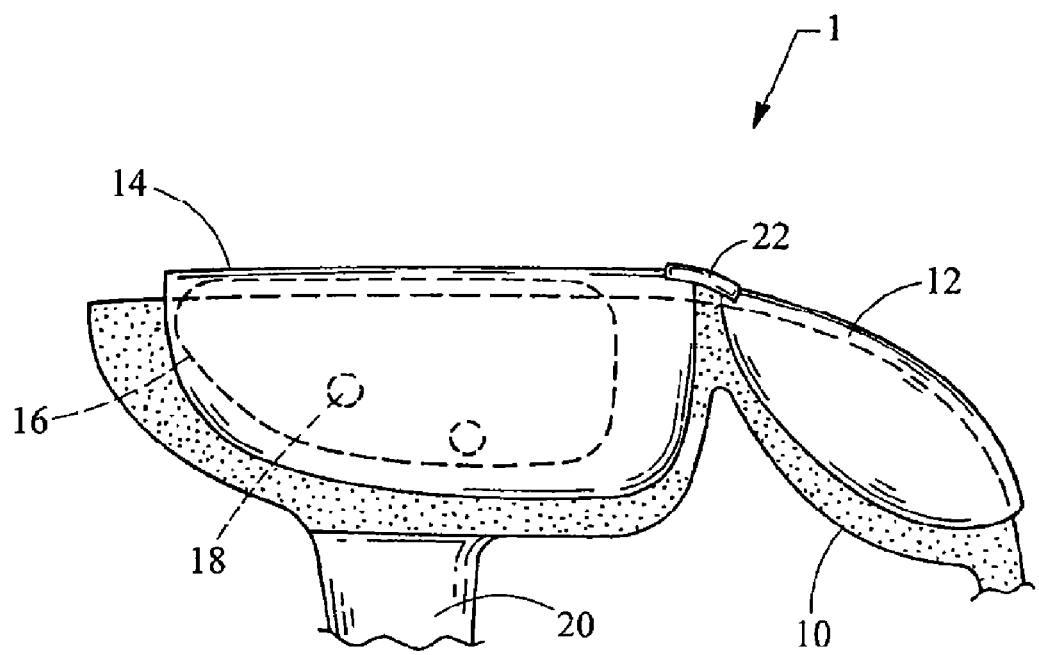
FIG. 1B illustrates a side view of the fixed plate and the slideable plate with the limb in a flexed state.

FIG. 1B illustrates the apparatus shown in FIG. 1A in a state where the joint of a limb, or body part to which it has been attached, has been flexed. The hinge 22 maintains substantially the same distance between adjacent ends of the fixed 12 and slideable 14 plates which it joins; however, the angle between the principal planes of the two plates becomes an acute angle, and the slideable plate 14 translates with respect to the slide plate member 16 and the sleeve 10, so as to accommodate this angular rotation. This translation may be seen by comparing the left hand end of the slideable plate 14 in FIGS. 1A and 1B with the left hand end of the sleeve 10.

The sleeve 10 may be either a portion of the surface of a cylinder as shown, or a complete cylinder, and the diameter of the cylinder may vary such that it approximately conforms to the shape of the body part to which it is intended to be attached. Alternatively, the sleeve 10 may be shaped to provide an underlying means of support to the plates 12, 14, 16 and attachment to the limb or body part by straps, by incorporation in an article of clothing or the like. The sleeve 10 may have different sizes, shapes and physical characteristics depending on the application and the type of protection desired. The sleeve may be made of stretch fabric, such as COOLMAX or perforated LYCRA (available from Invista, Wichita, Kans.), meshes, straps or bands, with open weave materials, neoprene or stretchable plastic, or a fabric chosen for strength, such as ballistic nylon. The surface of the sleeve may be continuous or perforated with holes of various sizes to increase ventilation. An energy absorbing material may be incorporated into the sleeve either as a surface layer or as a layer contained between two layers and located in the interior of the sleeve.

In the aspect where the sleeve is substantially a portion of a cylindrical shape, one or more straps 20 or other fastening device are provided to fasten the sleeve 10 to a body part. The straps may be made of ballistic nylon, plastic, stretchable fabric or the like, and may have adhering surfaces attached thereto or incorporated therein and be disposed such that complimentary adhering surfaces or self-adhering surfaces are each on straps connected to opposing sides of the sleeve. The straps 20 can be overlapped to secure the sleeve to the body part. Alternatively a loop may be attached to one side of the sleeve and a strap to the other side of the sleeve, such that the strap may be threaded through the loop, tightened manually and folded back on itself to secure the sleeve to the body part. Fastening materials may be VELCRO (available from VELCRO USA, Manchester, N.H.), DUALLOCK (available from 3M, St. Paul, Minn.), or the like. Other fastening methods may be used such as luggage snaps, where one or more of the mating components may be attached directly to sleeve or a plate. The sleeves may be separate, may be a single piece, multiple pieces joined together, or multiple separate pieces.

For use by humans, an adjustable fastening may be employed to accommodate the range of sizes of individuals. However when used in robotics, prosthetics and the like, a fixed mounting arrangement may be used and the plates or the plate slides may be mounted directly to a structural element, using structural attachments such as bolts, rivets, adhesive or the like, and the sleeve may be omitted. The arrangement may be incorporated in a prosthetic device.

The construction of the sleeve 10 is dependent on the type of protection desired, comfort considerations and economics. An energy absorbing material may be applied to the surface of the sleeve opposite to that of the body part or opposite a plate, or incorporated into the sleeve structure as an interlayer between outer sleeve layers. The energy absorbing material may be a gel, energy absorbing foam, memory foam, BROCK foam (available from Brock USA, Boulder, Colo.) or the like, and may serve to attenuate the energy transmitted from the plates to the body part. Additionally, the combination of the shape of the plates and the energy absorbing material may cooperate to distribute the transmitted force over a larger area than the input area, reducing the force per unit area being applied to the body part. In another aspect, the effect of the energy absorbing material may be to reduce the rate of application of energy with respect to the input rate.

The fixed 12 and slideable 14 plates may be constructed of energy absorbing or fracture resistant material, or a combination of both types. Plates may be molded to approximately conform to the shape of the body part to be protected. The plates may be a solid structure made of polyethelene, impact resistant plastic such as polycarbonate, polycarbonate or polypropylene resins which may impregnate a KEVLAR fabric (DuPont, Wilmington Del.), glass, carbon or boron, or similar fiber, a ceramic with an Ace backing laminate (available from Ace/Security Laminates, Ottawa, ON, Canada) or be a centrally disposed energy absorbing material of the same or similar types surrounded by a durable outer surface. Alternatively, all or part of the fixed 12 or slideable plates 14 may be made of a metal such as titanium or steel, or the like.

Where the fixed plate 12 is intended to be fixed to the sleeve 10, a side of the plate facing the sleeve may have a VELCRO or similar material affixed, with corresponding material affixed to the sleeve 10 so that pressing the plate 12 onto the sleeve will result in retention of the plate 12 in a fixed position with respect to the sleeve 10. The area to which the VELCRO is affixed is chosen in accordance with the desired strength of adhesion of the plate to the sleeve. The adhesion strength may be chosen such that the sleeve and plate are securely joined in normal use, but the sleeve and plate may be separated by the application of a force which may be injurious to the wearer, for example, by causing twisting of the limbs. Alternatively, the plate may be joined to the sleeve with rivets, adhesive or the like.

Figure 2B:
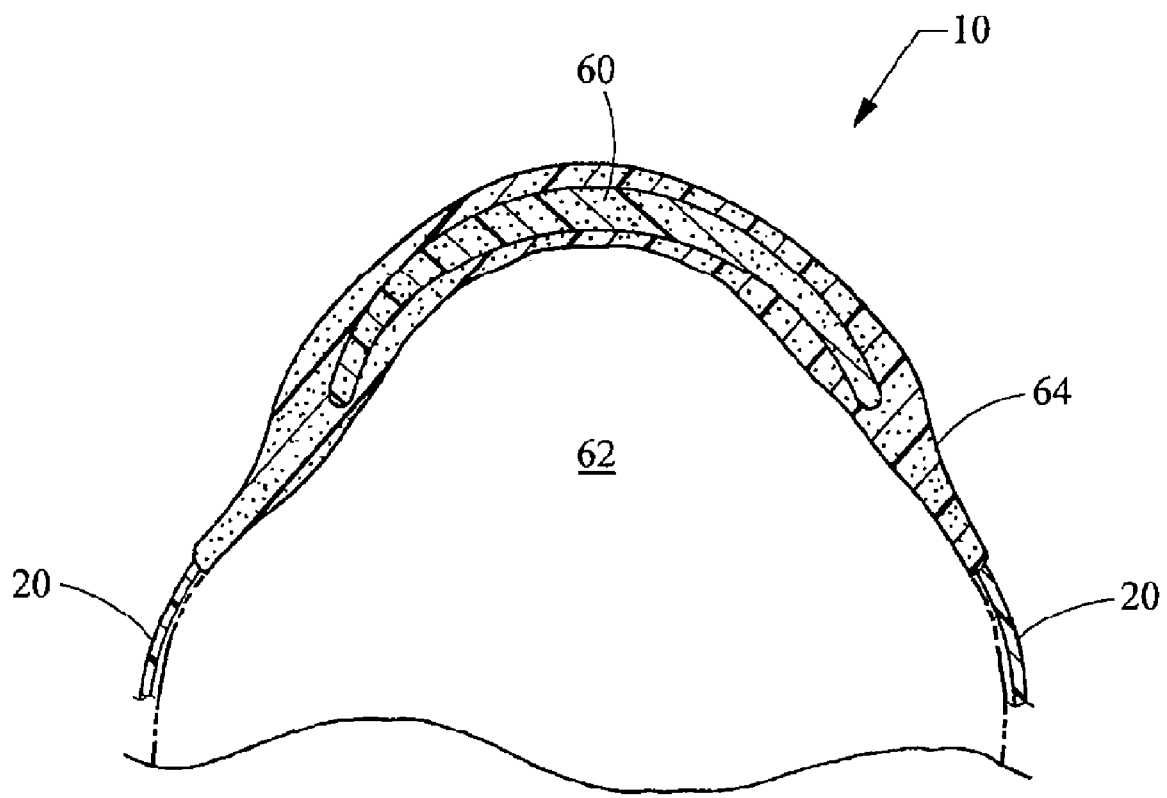
FIG. 2B illustrates a cross-section view of the sleeve and the limb at line B-B of FIG. 2A.

FIGS. 2A-H show a protective apparatus comprised of three plates, two of which are slideable, and which may be dimensioned such that the apparatus may be used for the protection of a bendable limb such as an arm or a leg. In this example, a leg exemplifies the body limb. FIG. 2A shows sleeve 10 shaped to approximately conform to the knee region of the leg, so as to protect the limb from predominantly frontal impact. The reliefs 60a, b in the sleeve 10 correspond to areas which will be substantially flexed or stretched when the joint is bent, and will lie approximately underneath the hinges 22 joining the plates. The sleeve may be formed of a multilayer assembly including an interior portion which may be a foam 60 or other energy absorbing or spreading material. Foam 60 may be covered with a fabric 64 or other material for protection as shown in FIG. 2B, to form the sleeve 10 having surfaces to which other elements of the apparatus, such as straps attachment points, and plate slide members can be attached, and to provide a suitable surface to contact a body part 62. The materials may be selected to have some porosity such that the sweat may transpire.

Figure 2C:
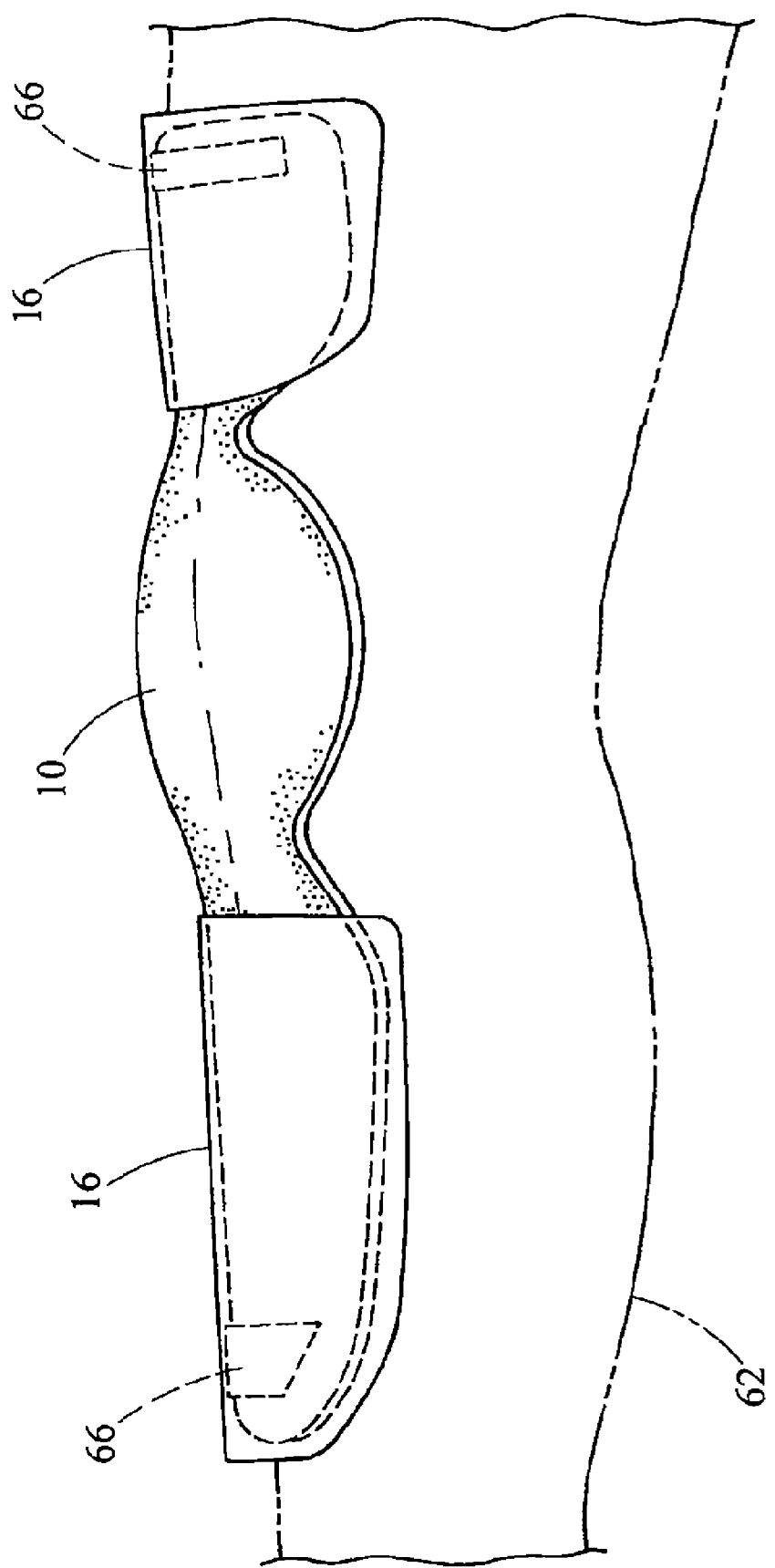
FIG. 2C illustrates a side view of an example of non-permanent attachment of plate slide members to the sleeve.
Figure 2D:
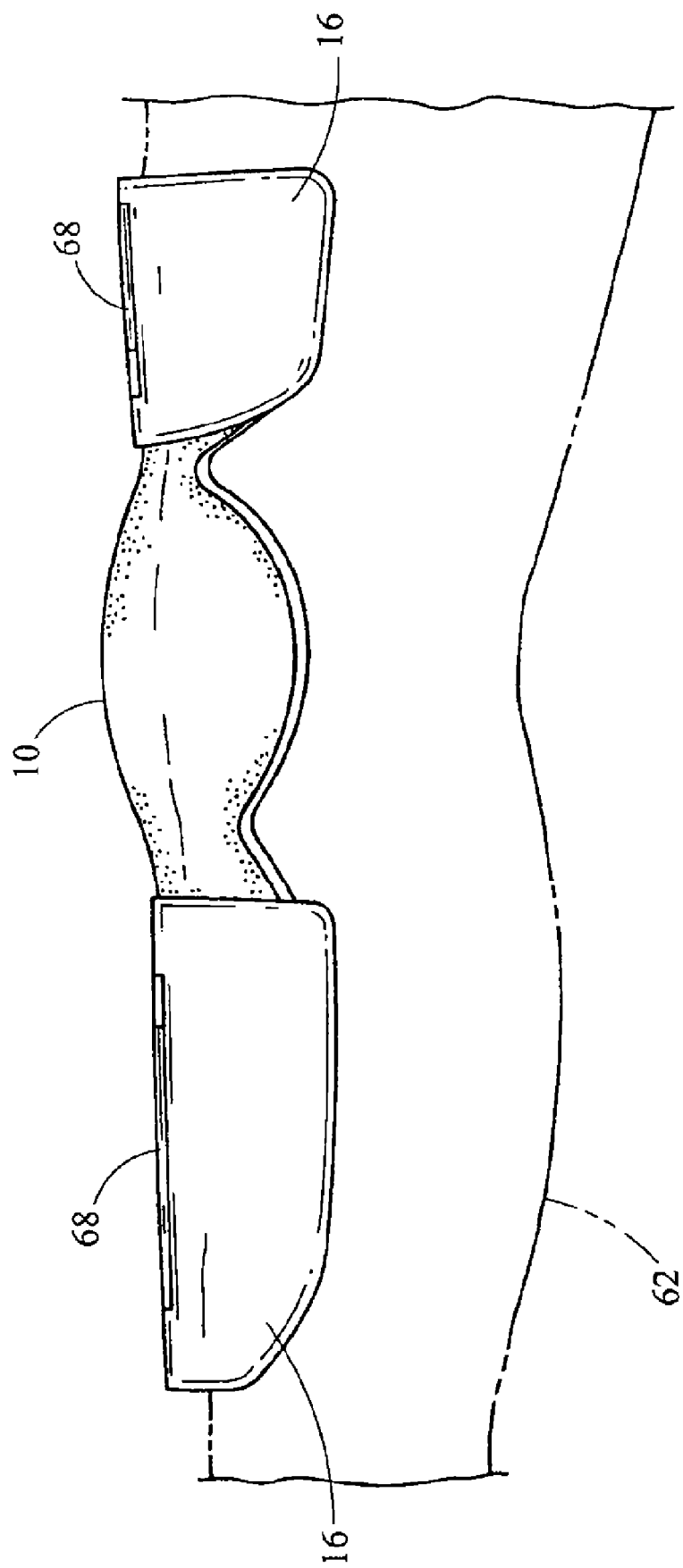
FIG. 2D illustrates a side view of an example of a captivating groove formed in each of the plate slide members.

The plate slide members 16 may be attached to the sleeve 10 using self-adhering material 66 such as VELCRO or DUALLOCK, applied to facing surfaces of the plate slide members 16 and the sleeve 10 as shown in FIG. 2C. By placing the attachment points 66 between the plate slide members 16 and the sleeve 10 at points distal from the flexing portion of the apparatus, a larger distance of the sleeve is permitted to stretch when the joint is bent, thus reducing the force required. Alternatively, the position of each of the attachment points can be selected to achieve a desired resistance to stretching. When plate slide members 16 are attached with a self-adhesive material, the application of a sufficient force in directions other than from substantially frontal impact may result in detaching the self-adhesive material portions which would contribute to reducing torsional forces on the limb. The plate slide members 16 are provided with a portion 68 adapted to interface with the slideable plates 14. In FIG. 2D, the portion 68 is shown as a channel, however the portion 68 may be a protrusion. Whether a protrusion or a channel, the portion 68 is dimensioned such that a captivation structure is formed between the plate slide member 16 and a slideable plate 14. The portion 68 may extend for either part of the length of the plate slide member 14, or to one or both of the ends of the plate slide member 14.

FIG. 2E shows the assembly with straps 20 for attaching the apparatus to the limb 62 attached to the sleeve 10. The straps may be a continuation of a surface 64 of the sleeve 10, or be sewn or attached by rivets or other fasteners to the sleeve. Also shown is a further detail of the plate slide member portion. The length of the portion 68 may be greater than that of a corresponding mating portion 70 of the slideable plate 14, which is a part of, or attached to, the slideable plate 14. For clarity, only the mating portion 70 of the slideable plate 14 is shown in FIG. 2E, positioned corresponding to an un-flexed state of the leg. The length of the portion 68 may be greater than that of the portion 70 by a distance 68a, representing at least the distance that the slideable plate 14 is permitted to slide when the joint is in a fully flexed state.

Figure 2F:
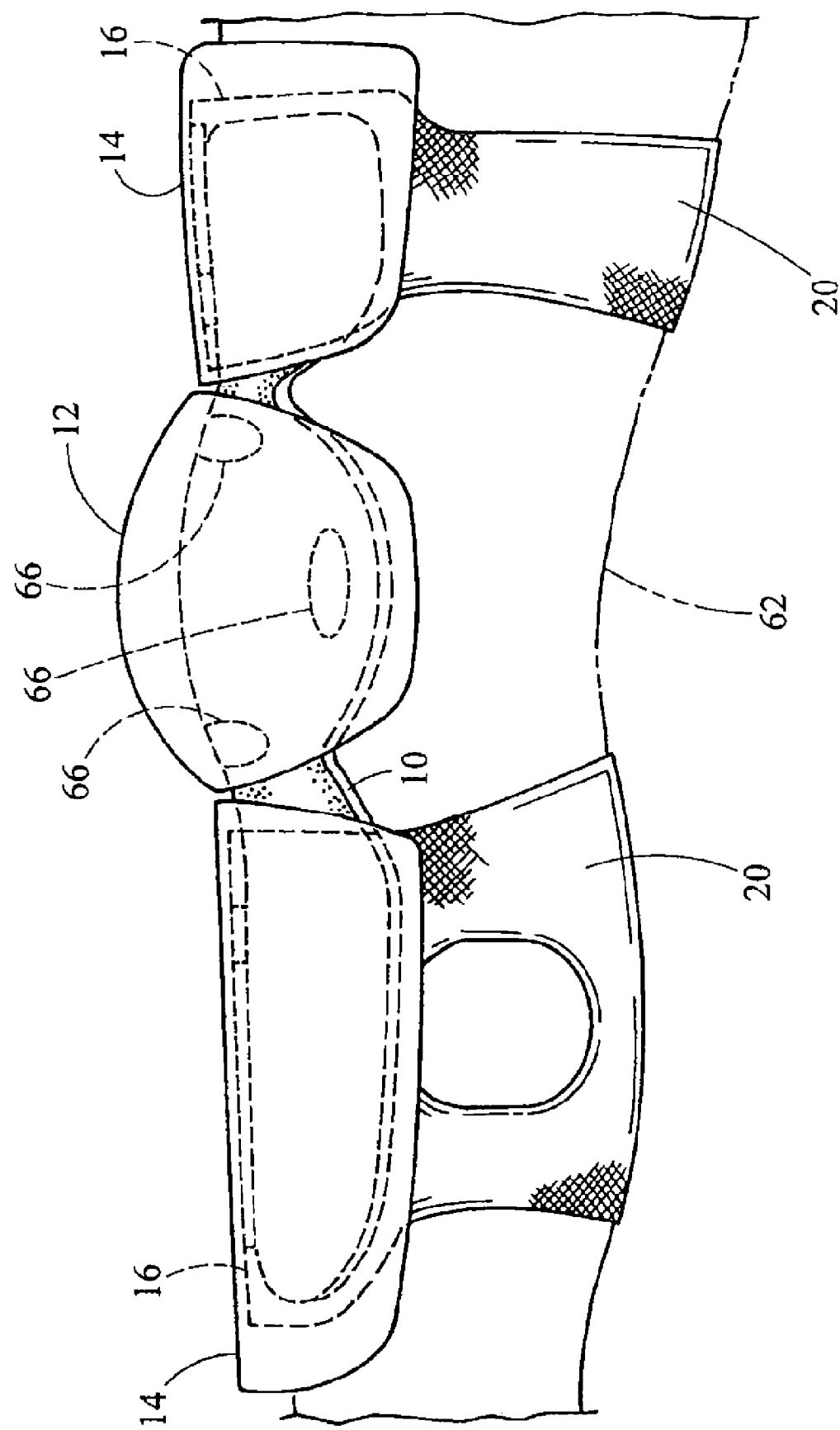
FIG. 2F illustrates a side view of slideable plates captivated by plate slide members, and a fixed plate non-permanently attached to the sleeve with self-adhesive strips.
Figure 2G:
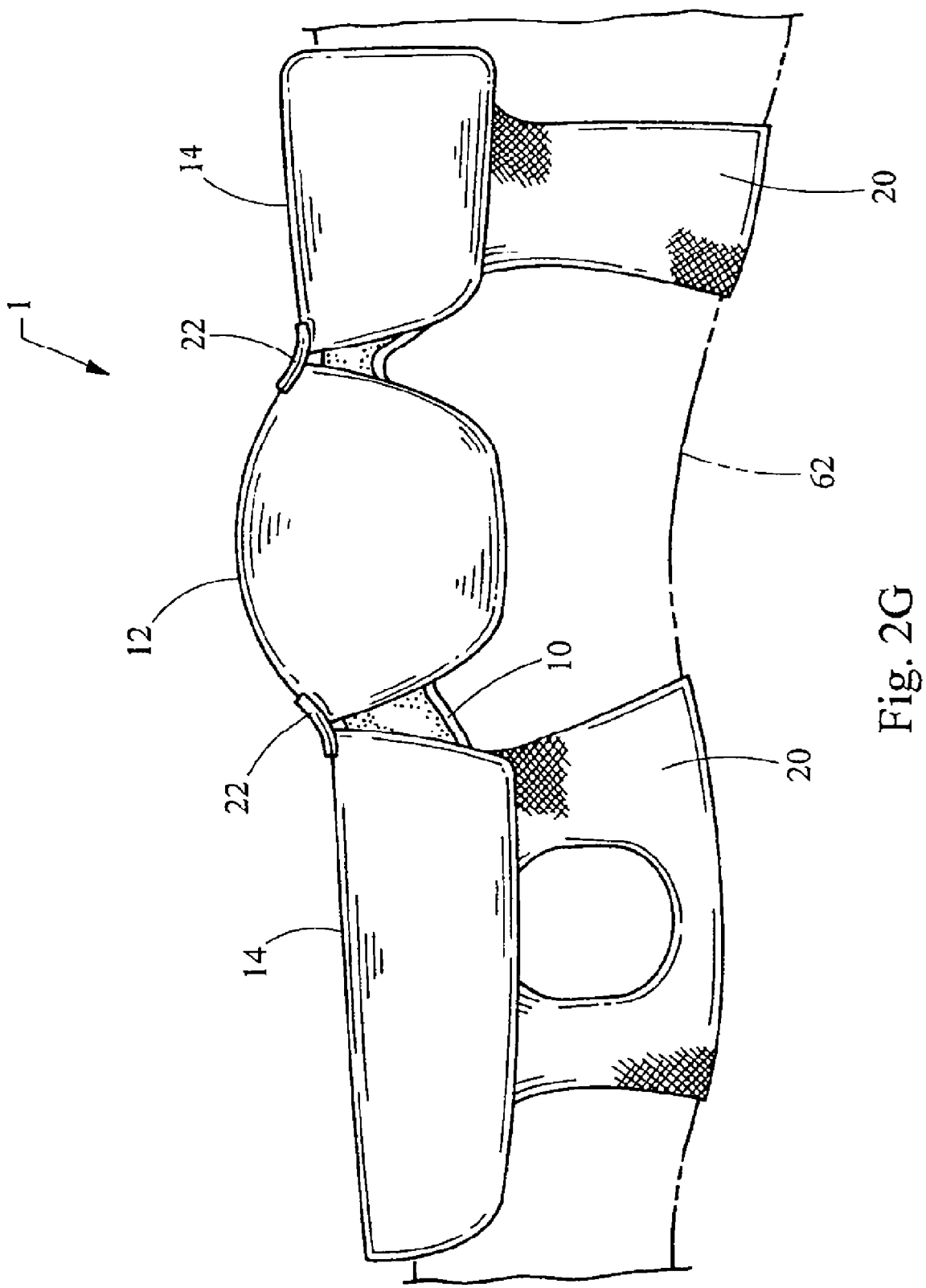
FIG. 2G illustrates a side view of an example of the slideable plates connected to the fixed plate with hinges.

FIG. 2F shows the assembly with the slideable plates 14 and a fixed plate 12 in a captivated position, and with the limb in a straight state. Also illustrated is the attachment of the fixed plate 12 to the sleeve 10 using a plurality of adhesive or self-adhesive pads 66. The combination of the sleeve 10 and the straps 20 tends to hold the fixed pad 12 in position over the joint both in the straight state and in the flexed state. FIG. 2G shows an outer side view of the assembly 1, where the slideable plates 14 are joined to the fixed plate 12 by hinges 22 or other similar flexible or bendable elements.

Figure 2H:
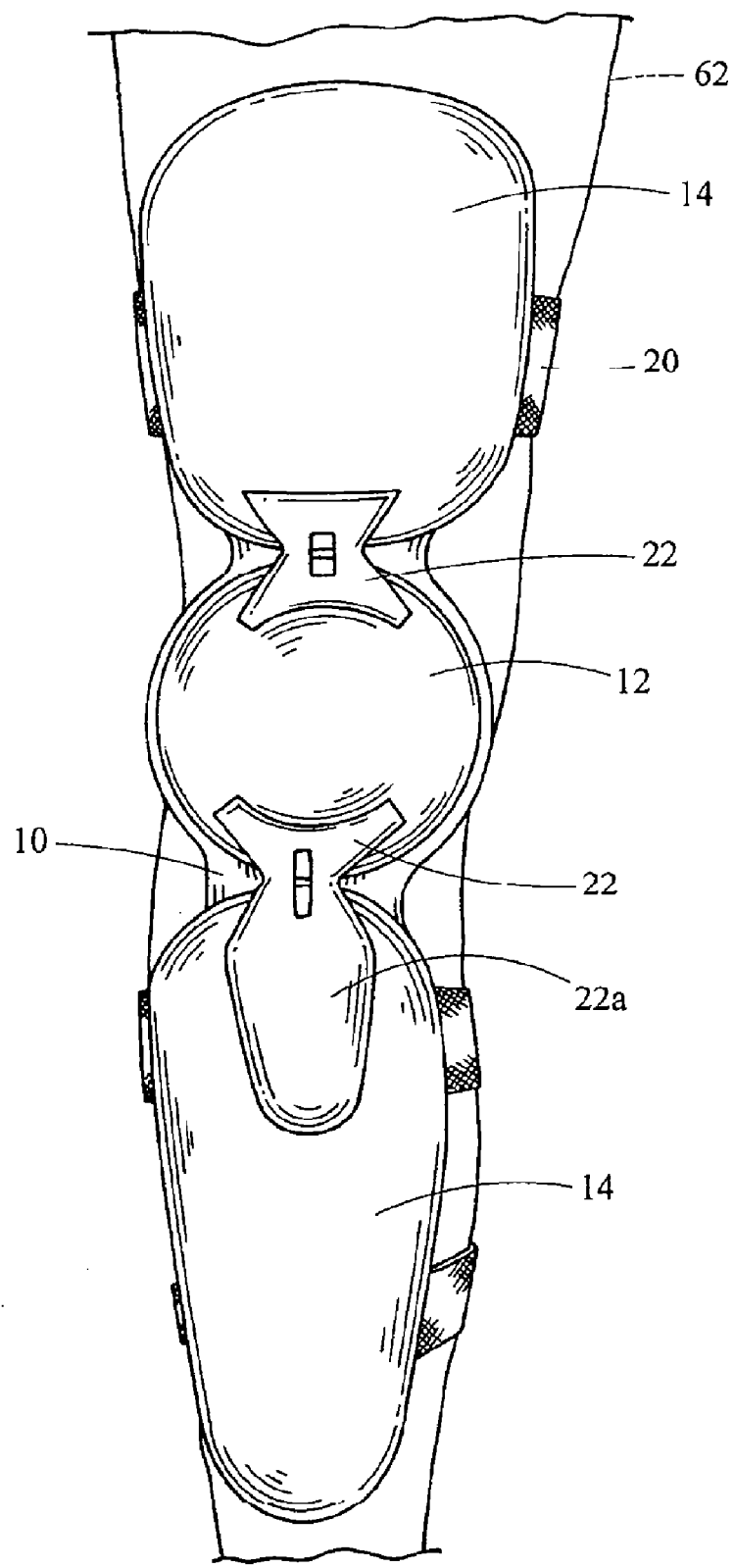
FIG. 2H illustrates a frontal view of assembly of FIG. 2G.

FIG. 2H is a front view of the apparatus 1 applied to a leg, where the leg is in a straight state. The hinges 22 join the slideable plates 14 to the fixed plate 12. In this example the hinge 22 may be over-molded on the plates. It may also be attached by rivets, screws, or adhesive, through holes made in the plates, by mechanical interlocking, or the like. The hinge 22 may also have extensions 22a onto the surface of the slideable plate 14 and the fixed plate 12 to both increase the attachment strength and to form part of a cushioned kneeling platform when the limb is flexed, and the shin portion is in contact with the ground or other surface. Such extensions 22a may also serve to flatten a portion of the contact area between the slideable plate and the ground so as to increase the stability of a wearer when in a kneeling position. The connections between the portions of the hinge 22 on each of the slideable plate 14 and the fixed plate 12 may be one or more flexible strips or straps so as to minimize the force needed to bend the apparatus in the region between adjacent ends of plates. In another aspect, a strengthening material such as KEVLAR may be laminated into the hinge 22 for reinforcement and to limit the stretching of the hinge while preserving flexibility for bending.

Figure 3A:
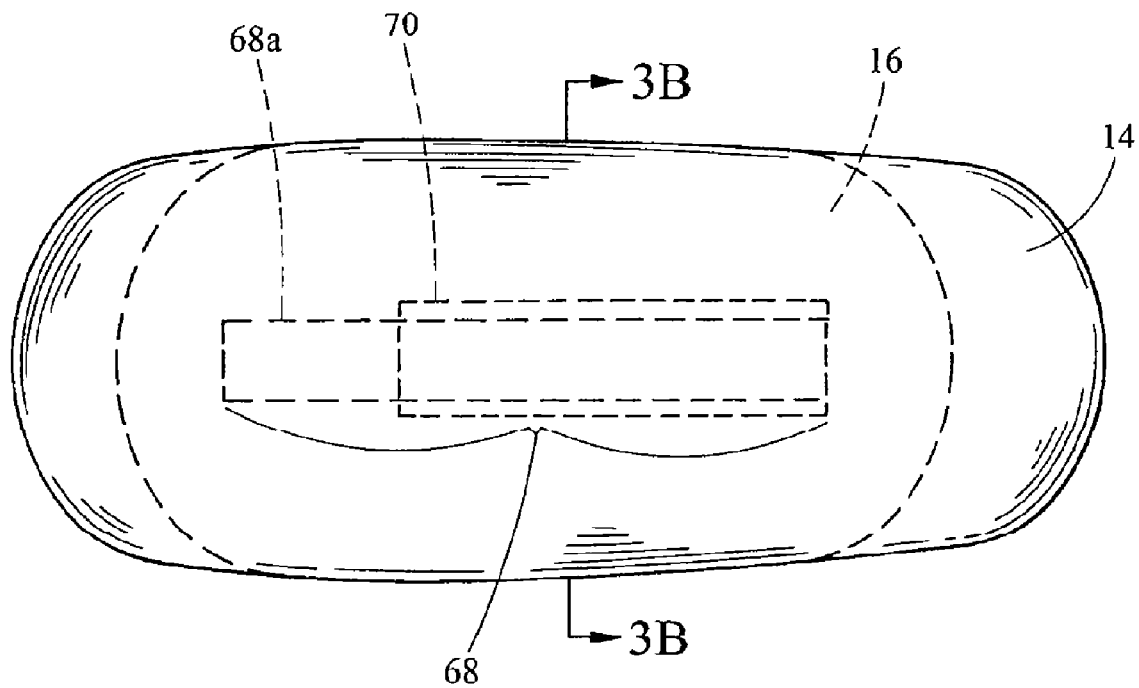
FIG. 3A illustrates a frontal view of the slide plate and plate slide member of FIG. 2G.
Figure 3B:
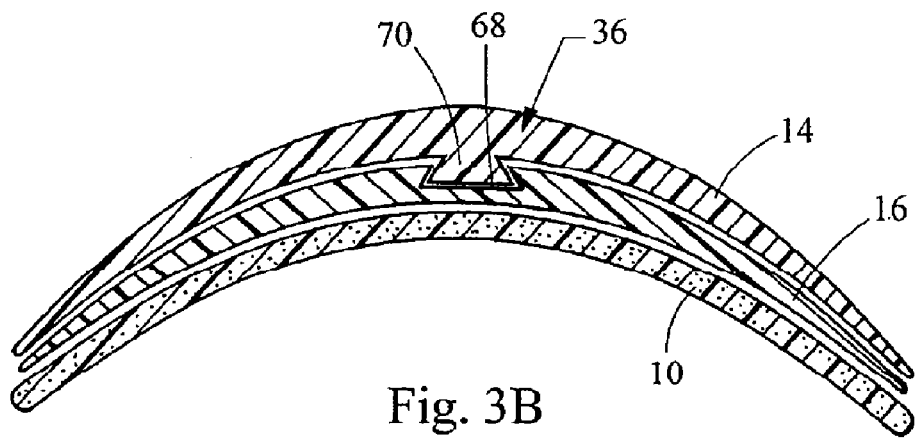
FIG. 3B illustrates a cross-sectional view of an example of captivating the slideable plate to the plate slide member.

The attachment of the slideable plate 14 to the plate slide member 16 may be accomplished by a variety of sliding joints, an example of which is shown in FIG. 3. In FIG. 3A, a plan view of a slip joint is shown viewing from the upper surface of the slideable plate 14. FIG. 3B shows a cross-section of the joint at section B-B. The slideable plate 14 may be molded to have a protrusion 70 extending from the underside thereof as an engaging structure, where the protrusion 70 has the form of a trapezoid or similar shape, and the plate slide member 16 has a complementary-shaped recess 68 to accommodate and captivate the protrusion 70. The same cross-sectional shapes may extend along the portion of the slideable plate 14 and plate slide member 16 or only a part thereof. When the recess 68 does not extend for the full length of the plate, the recess 68 is sufficiently long such that the protrusion 70 may slide for a distance along the recess 68 to accommodate the flexing of the limb. In an aspect where the recess 68 extends so that it reaches the end of the slide plate member 16 distal from the hinge 22, the protrusion 70 may be permitted to extend past the end of the slide plate member 16 when the leg is in a straight state, and in this circumstance, the length of the recess 68 need only be long enough such that the slide plate 14 may slide towards the hinge 22 when the limb is flexed.

The plate slide member 16 and the slideable plate 14 are shaped so as to substantially conform to the shape of the limb 62, and while the FIG. 3 may show a cross-sectional symmetry about a center line, the shape of the plate slide member 16 and the slideable plate 14 may be somewhat asymmetrical with respect to the center line, or along the length of the elements; however, the protrusion 70 and the accommodating recess 68 are substantially symmetrical with respect to the center line such that the slideable plate 14 may translate along its length with respect to the plate slide member 16. To the extent that the protrusion 70 and the recess 68 are not symmetrical with respect to the center line, each of the structures should have a substantially identical radius of curvature so that the slideable plate 14 may slide with respect to the slide plate member 16.

As shown in FIG. 3B, the radius of curvature of the slideable member 14 and the plate slide member 16 for facing surfaces thereof may be such that a clearance between the slideable plate 14 and the plate slide member 16 exists along substantially the entire overlap portion (except for the protrusion 70 and recess area 68). The radius of curvature of the slideable member 14 may be less than that that of the plate slide member 16 so that the gap between the two decreases as the distance from the captivating region increases, and the slideable plate 14 and the plate slide member 16 may be permitted to touch near the outer edges thereof. Such a configuration may act to reduce the amount of dust and dirt that may be able to intrude between the two plates. Other shapes having similar effect are possible. Ridges 17 or bumps disposed as ridges, or distributed on the surface of either the slideable plate 14 or the slide plate member 16 may be used to reduce the contact area between the two plates when the plates are displaced to contact each other by an external force.

The captivating connection 36 between the engaging structure and the captivating structure is dimensioned such that the slideable plate 14 and the plate slide member 16 may slide freely with respect to each other along the length of each part, while retaining the parts together in a direction perpendicular to the slideable plate 14. The slidability may be improved by the application of low friction coatings or lubricants.

Figure 3C:
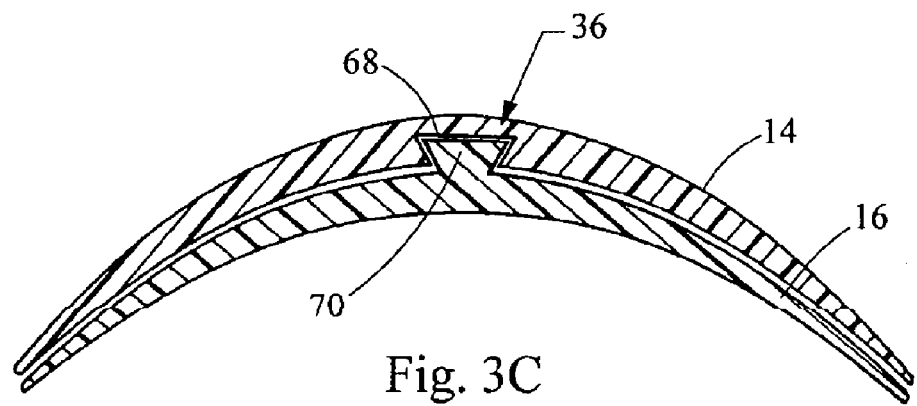
FIG. 3C illustrates a cross-sectional view of another example of captivating the slideable plate to the plate slide member.

While the protrusions 70 have been shown on the sliding member 14 and the recesses 68 on the plate slide member 16, the configuration may be interchanged in whole or in part with equal effect as shown in FIG. 3C.

The materials and dimensions of the protrusion 70 and the recess 68 may be selected such that the application of a force substantially perpendicular to the sliding connection and parallel to the to the surface of the sliding plate (shown by the arrow labeled FORCE in FIG. 3C) which may be sufficient to cause physical injury to the wearer, results in the separation of the sliding plate 14 from the plate slide member 16. This separation may be effected either in a manner which permits the plate to be re-engaged with the slide member, or where either the plate or slide member is damaged in the process of separation.

Figure 4A:
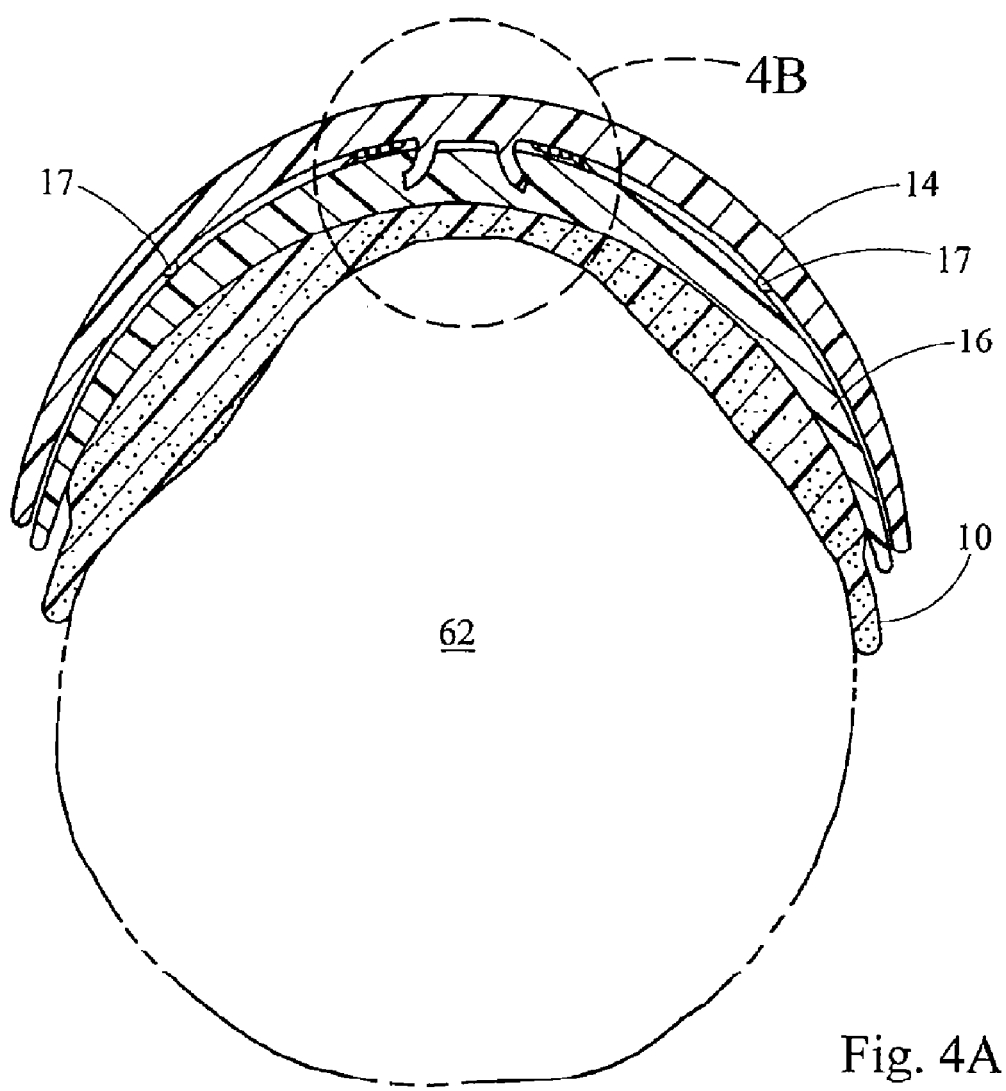
FIG. 4A illustrates a cross-sectional view of yet another example of captivating the slideable plate to the plate slide member.
Figure 4B:
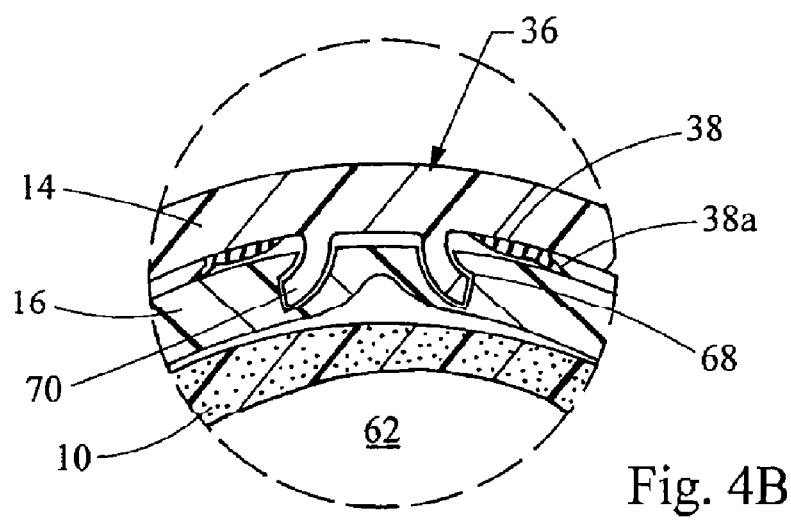
FIG. 4B illustrates a detailed cross-sectional view of the arrangement of FIG. 4A.

In another example of the captivation of the slideable plate 14 and the plate slide member 16, shown in FIG. 4A, the captivation region 36 includes a plurality of protrusions 70 and a corresponding plurality of recesses 68 disposed such that the recesses 68 and the protrusions 70 may engage to captivate the slide plate 14 to the plate slide member 16. Engagement of the protrusions and the recesses may require the flexing of the protrusions and may require the flexing of the side walls of the recesses. Details of the captivation region 36 are shown in FIG. 4B, where additional structures 38 are disposed approximately symmetrically to the protrusions 70, and extend into the gap between the slide plate 14 and the plate slide member 16. A flexible extension of the structure 38, in the form of a flap 38a, is dimensioned such that it approximately closes the gap, and serves to limit the access of dust and other contaminants to the region 36 in which the captivation occurs. The structure 38 may be molded as part of the slide plate 14, or be separately applied with an adhesive or the like, and may of the same material as the surface of the slide plate 14 or another flexible material. Alternatively, the structure 38 may be attached to the plate slide member 16 and extend towards the slide plate 14. The structure 38 may also be sized and positioned such that sufficient pressure orthogonal to the surface of the slideable plate 14 causes contact between an inner surface of the slideable plate 14 and an opposing surface of the plate slide member or the structures 38, thus restricting the sliding motion that can be imparted by external forces. Alternatively, such a material may be inserted between opposing portions of the protrusions 70 and the recesses 68. The interface material 38 may be arranged either continuously or in one or more segments along the length of the assembly depending on the clearances, the flexibility of the slideable plate and the plate slide member, and the degree of resistance to external sliding forces desired.

In FIGS. 3 and 4, the slideable plate 14 may be urged to move with respect to the plate slide member 16 by a force applied along the length thereof through the hinge 22 as the limb joint is flexed. The change in angular relationship between the plates (that is a fixed plate 12 and a slideable plate 14, or between two slideable plates 14) results in a force directed at least along the length of the protrusion 70, causing the slideable plate 14 to move slideably with respect to the plate slide member 16. The slideable plate 14 will have moved a maximum amount with respect to the plate slide member 16 when the limb has been flexed such that a minimum acute angle has been reached. When the limb is returned to a straight position, the force of gravity or a force imparted by the hinge 22 tends to return the slideable plate 14 to a position with respect to the plate slide member 16 which previously obtained when the limb was in a straight state.

Figure 5A:
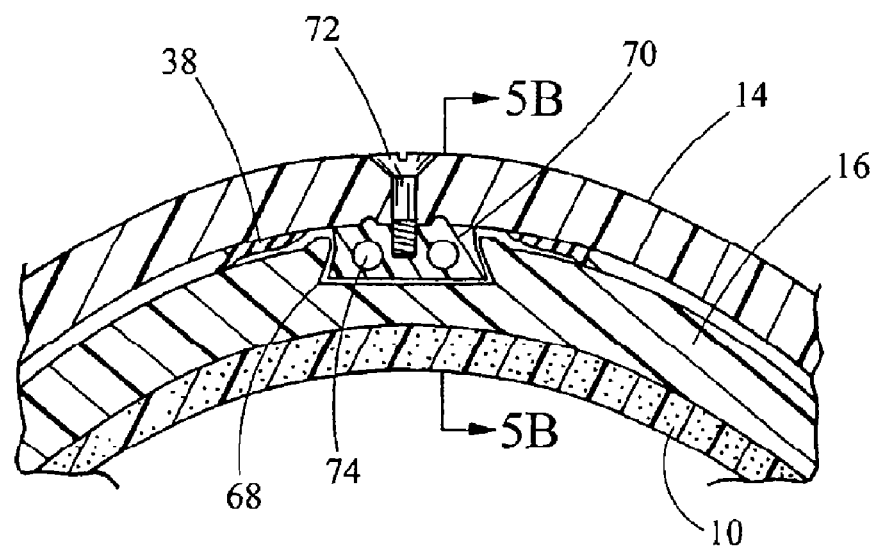
FIG. 5A illustrates a cross-sectional view of still another example of captivating the slideable plate to the plate slide member, showing a spring return mechanism and a means for adjusting the relationship of the slideable plate and the plate slide member.
Figure 5B:
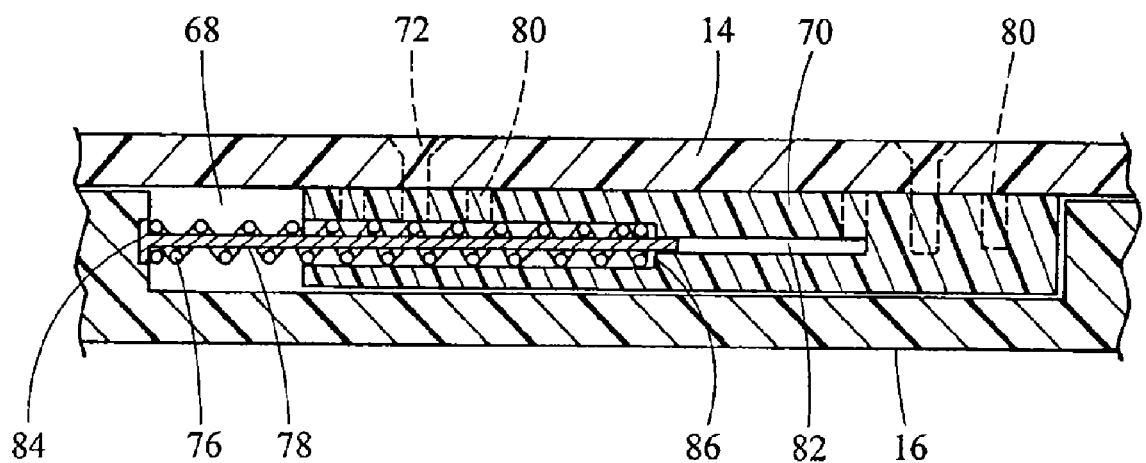
FIG. 5B illustrates a longitudinal cross-section along line B-B of FIG. 5A.

Alternatively, the slideable plate 14 may be urged to return to this position by a spring. In an example, shown in FIG. 5A, the protrusion 70 is formed by a separate piece, although it can be integral to the slideable plate 14. The protrusion 70 is attached to the slideable plate 14 by one or more screws 72, and the protrusion 70 has holes 74 formed longitudinally therein. FIG. 5B shows a cross-section at line B-B which is approximately the centerline of the assembly. The protrusion 70 is affixed to the slideable plate 14 by screws 72. In an aspect, more than the required number of mating holes 80 are provided in the protrusion 70, spaced such that the protrusion 70 may be fixed at one of a plurality of locations along the centerline of the assembly, so as to provide for an adjustment of the position of the slideable plate 14 with respect to the slide plate 16. Each of the longitudinal holes 74 is sized so as to as to receive a spring 76, filling a depth between an end 84 of the channel 68 and a narrowing 86 of the longitudinal hole 74. The spring 76 may be fitted over a mandrel 78 disposed between the end 84 and extending into a further extension 82 of the hole 74, or some other means of supporting the ends of the mandrel 76. The mandrel 76 has the effect of supporting the spring 78 so that the spring 78 does not buckle under pressure. The slideable movement of the slideable plate 14 with respect to the plate slide member 16 has the effect of compressing the spring 78 as the protrusion 70 moves towards the end 84 of the channel 68. This creates a restoring force which tends to urge the slide plate 14 to return to the position shown in FIG. 5B when the limb is straightened. Other means of urging the slideable plate 14 to return to a desired position with respect to the plate slide member 16 may be used including an air spring, or a pneumatic cylinder.

Where the term "center line" is used, it is understood to mean a line approximately longitudinally disposed with respect to a limb, and approximately equidistant from the edges of a slideable plate in a direction transverse to the direction of motion thereof. An exact centerline in a linear sense is not implied as the shapes of the plates, the plate slide member, and the sleeve may have some asymmetry in order to conform to the shape and orientation of the various portions of the limb.

Figure 6A:
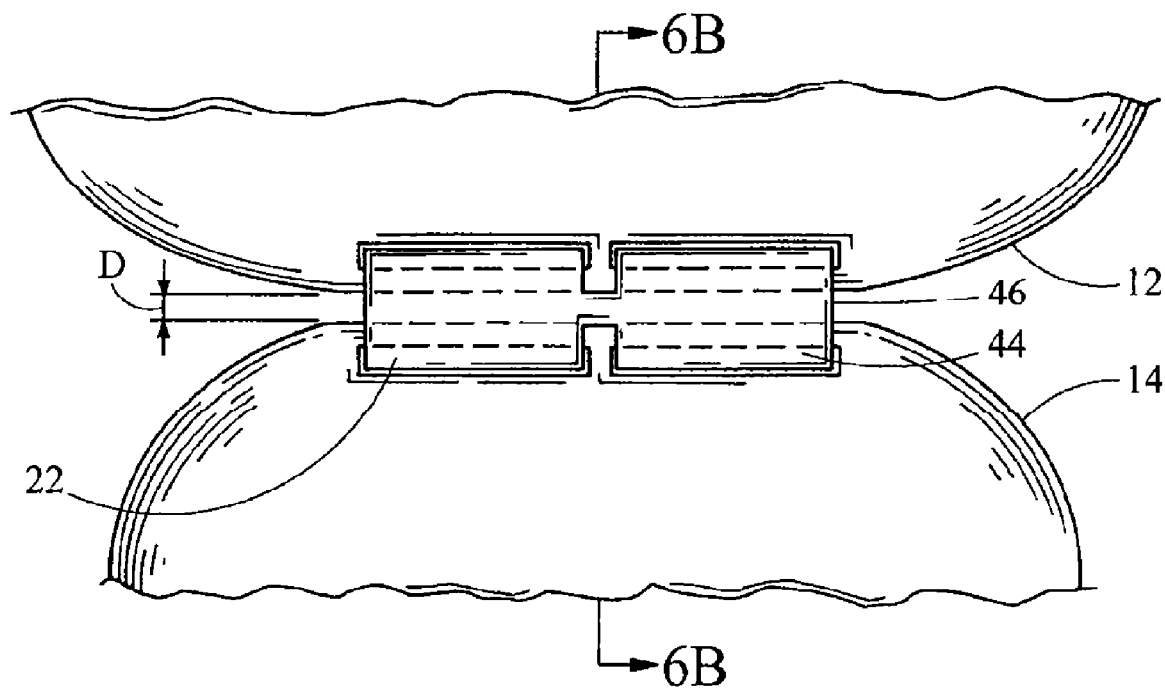
FIG. 6A illustrates a detail of FIG. 2H including a hinge for connecting a fixed plate and a slideable plate.
Figure 6B:
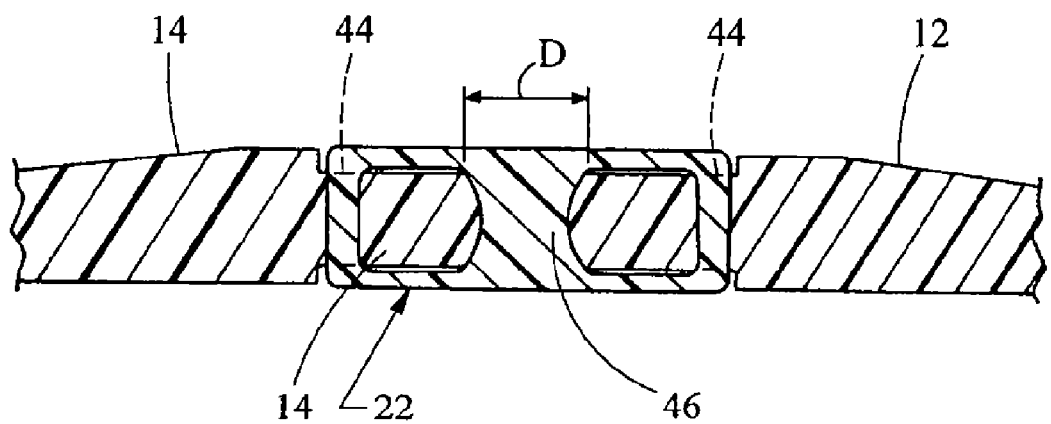
FIG. 6B illustrates a longitudinal cross-section along line B-B of FIG. 6A.

The slideable plate 14 and the fixed plate 12 are joined together by a strap, hinge, ligature, torsion element or the like so that the relative distance between adjacent ends thereof is substantially fixed, while the angular relationship of the adjacent plates may vary. An example of a joint with a hinge is shown in FIG. 6A. In this example, a fixed plate 12 and a slideable plate 14, or two slideable plates, is joined by a hinge element 22. One or more slots 44 are formed in the plates and the plates 12, 14 are separated by a distance D. A flexible material 46 is over-molded on the plates 12, 14 so as to fill the area between the adjacent ends of the plates 12, 14, and may cover all or part of the plate area between the plate end and the slot 44, and connect through the slots 44, as shown in FIG. 6B, which is a cross section of the joint at line B-B, so that the upper and lower surfaces of each plate are each partially contained in the volume formed by the molded flexible material. In this example, when the joint bends, the portion of the flexible material 46 disposed between the adjacent ends of the plates flexes to permit two plates to rotate with respect to each other and accommodate the motion of the joint. The flexible material 46 may encapsulate a strengthening material such as KEVLAR, which may be used to increase the durability of the joint, or to reduce stretching, which would have the effect of permitting the distance D between the plates 14, 12 to increase.

Figure 7A:
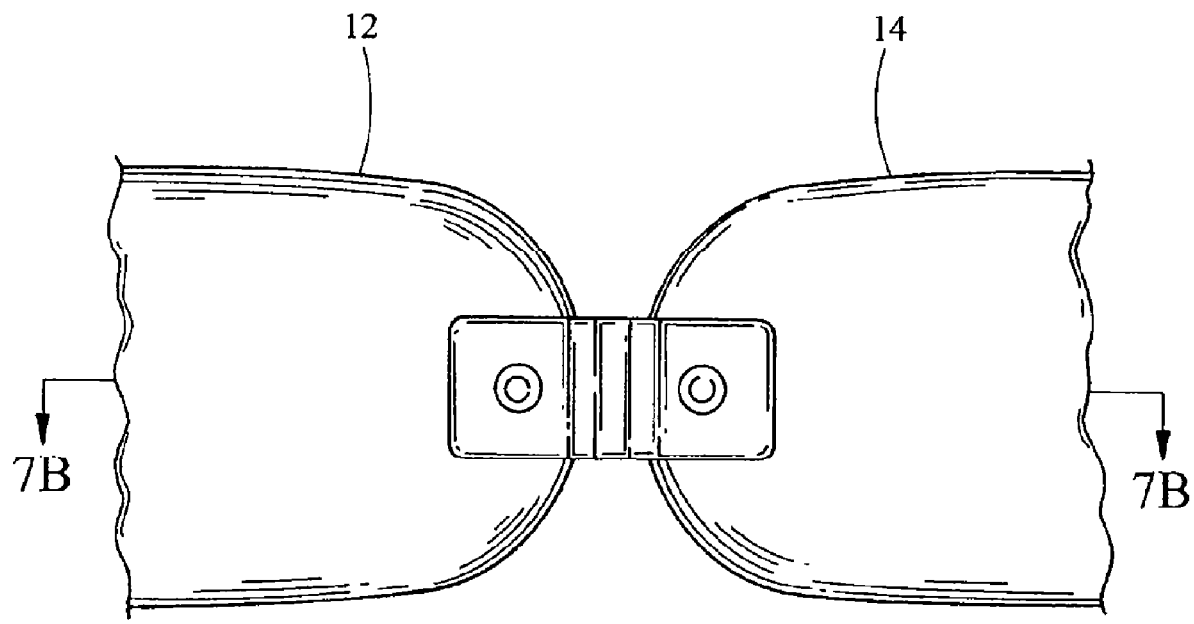
FIG. 7A illustrates a frontal view of an example of a hinge joining two plates, in the form of a strap or bar.
Figure 7B:
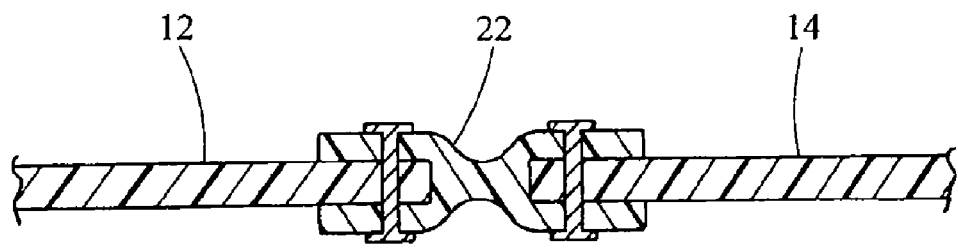
FIG. 7B illustrates a longitudinal cross-section along line B-B of FIG. 7A.
Figure 8A:
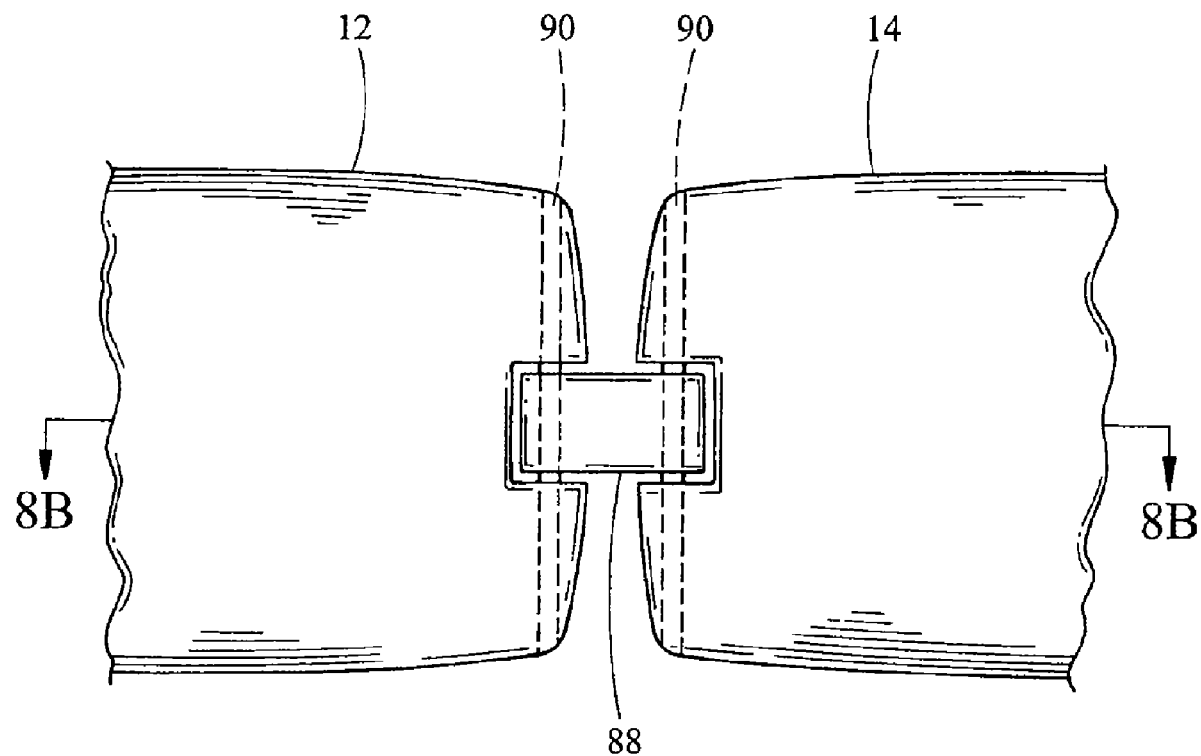
FIG. 8A illustrates another example of a hinge joining two plates, which includes a bar which may exhibit rigidity disposed on journals.
Figure 8B:
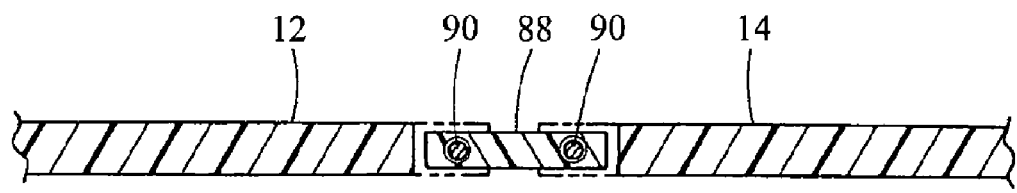
FIG. 8B illustrates a longitudinal cross section along lime B-B of FIG. 8A.

FIGS. 7A, B and FIGS. 8A, B show alternative versions of a hinge connection between the plates. From these examples, it may be understood that a hinge is meant to represent any connection between two plates having the property that the plates are joined together with a substantially fixed distance between adjacent ends; that the connected plates may rotate with respect to each other to transform from a substantially straight alignment to an alignment where an acute or obtuse angle is formed therebetween. Such an arrangement is not meant to preclude some angular motion about an axis orthogonal to the principal axis of rotation, such that the apparatus may twist to a limited extent. In the example of FIG. 8, it may be seen that this hinge property can be obtained by a member 88 which may be rigid or flexible with one or more pins 90, disposed such that the member 88 is journaled by the pin or pins 90. In another aspect, the rigid member 88 may be fixedly attached to, or formed integrally with, a plate.

The angular rotation permitted may be greatest about an axis that is perpendicular to the direction of sliding of the slideable plate and parallel to the surface of the plate. This corresponds to the articulation of, for example, a knee or elbow joint. Rotation of the plates about an axis orthogonal to the first axis also may be permitted to accommodate rotational motion of the joint.

As shown in FIG. 2H, the two plates may be over-molded with a flexible material on all or part of the surfaces of the fixed 12 or slideable 14 plates such that a web connection is made between the two plates. Such over-molding may be performed where the plates are also connected with a strap or ligature or hinge. The hinge may be as single piece molded from a flexible material such as thermoplastic elastomers or silicon rubber, or the plates may be connected by a conventional hinge made from metal or plastic.

The operation of the apparatus when applied to a leg 62 is shown in a side view, in FIG. 9. FIG. 9A shows the leg with the joint in an un-flexed state. An upper slideable plate 14*b* and a lower slideable plate 14*a* are each joined to a fixed plate 12 with hinges 22. The fixed plate 12 is disposed such that it is positioned over the kneecap when the apparatus is in position and the leg is approximately straight. Straps 20 hold the apparatus in position with respect to the leg 62. Each of the slideable plates 14 is attached to the fixed plate by a hinge 22. The underlying plate slide member 16 for each of the slideable plates 14*a, b* is not shown in this figure. When the knee is partially bent as shown in FIG. 9B, the slideable plates 14*a, b* have been rotated angularly with respect to each other to conform to the motion of the limb. To accommodate this angular rotation, the slideable plates 14 move longitudinally (that is, slide parallel to) with respect to the leg portions to which they are attached, by sliding with respect to the plate slides members 16. This may be seen by comparing the relationship of the slideable plates 14*a, b* to the upper 10*b* and lower 10*a* ends of the sleeve 10. FIG. 9C illustrates the knee joint in a substantially fully bent position, and it may be seen that the slideable plates 14*a, b* have continued to translate with respect to the sleeve ends 10*a, b* so that the angular relationship between the slideable plates 14*a, b* conforms to that established by the bent limb. The fixed plate 12 remains in position above the kneecap, such that an impact directly on the kneecap will be absorbed by the fixed plate 12.

The protection device is shown as being applied to a knee; however other joints such as the elbow or ankle may be similarly protected. An upper slideable plate and a lower slideable plate are each connected to a fixed plate disposed therebetween, such that the adjacent end of each of the slideable plates is connected to the fixed plate. The upper and the lower slideable plates are attached to upper and slide plates respectively. The upper and lower sleeve may have straps or other means of fastening the sleeves to the limbs or other body part. A central sleeve disposed between the upper and lower sleeves may be provided for the fixed plate.

In another aspect, one or more sleeves may be joined together or fabricated with at least one common layer to approximately maintain the positioning and spacing of the slideable plates. The common layer or material joining the sleeves may be selected so as to have an elastic property such that the material stretches easily when the joint is bent, reducing the effort necessary to bend the joint. Alternatively, the sleeve may be partially cut transverse to the limb, or some of the layers cut, or the material be designed to stretch in a portion joining two sleeves. Joining the sleeves may orient the apparatus 1 with respect to the limb, and positions the slideable members so that the device may be applied to the limb rapidly. The spacing between the adjacent ends of the plates when the device is detached from the limb is selected so as to assist in the orientation of the device with respect to the limb for a representative user when applying the device to the limb. Alternatively, the apparatus may be adapted to meet ergonomic requirements such as by the means shown in FIG. 5, where the position of the slideable plate 14 with respect to the plate slide member 16 may be adjusted by means of the placement of the attachment screws 72.

In another aspect, the size, construction and attachment of the plates is varied depending on the expected end use, and to accommodate the specific requirements of the design, such as area to be protected, expected impact force parameters, including force direction and time profile, durability, maintainability and ergonomic factors. Similarly, the means of attachment of the plates to the sleeve is selected to facilitate the use of the device for each specific intended purpose. More than one attachment means may be suitable for each intended use and may be selected to suit the preference of the user.

In this manner, it may be seen that the fixed and slideable plates and the associated impact absorbing aspects of the sleeve permit the joint to flex, where the force necessary to move the parts of the apparatus is mainly to overcome frictional forces between the slideable plates and the plate slide member. The friction may be minimized by appropriate sizing of the engaging and captivating structures, and the length and shape thereof, the selection of materials, and the use of surface coatings. Where sleeves are individually associated with each connected plate, the sleeves may move rotationally with the limb motion, without additional force input. When the sleeves are connected to each other as shown in FIG. 2, some additional force may be necessary at some point in the joint motion to stretch the material joining adjacent portions of the sleeves; however as the material joining the portions of the sleeves may be made to yield with little force, such additional force can be minimized.

The sliding of the slideable plates 14 with respect to the sleeve 10 shown, for example, in FIG. 9 is seen to expose some of the sleeve 10 such that an impact may be transmitted directly to the sleeve 10 without an intervening plate 12, 14. Depending on the specific application, such a situation may be permissible. However in applications where this may be undesirable, an auxiliary plate 102 may be disposed in the exposed area, sized and located such that the slideable plate 14 slides over or under the auxiliary plate 102, as required. FIG. 10A shows such a configuration in a partial view of one slideable plate 14 and one auxiliary plate 102, when the joint is in an un-flexed state. The auxiliary plate 102 may be a fixed plate 12, or another plate having no hinge connection to another plate. As shown, the auxiliary plate 102 is fixed to the sleeve 10 by one or more fasteners 104, which may be rivets, bolts, patches of self-adhesive material or the like. Alternatively the auxiliary plate 102 may be captivated between an outer covering 64 of the sleeve 10 and an energy absorbing interior 60. The overlapping plates may be arranged in a complimentary manner to preserve a low thickness profile while maintaining a continuous protective surface. In another aspect, the auxiliary plate 102 may be omitted by lengthening the slide plate 16 beyond the end of the slideable plate 14, or by extending the slideable plate 14 beyond the end of the slide plate 16. In another aspect the auxiliary plates 102 may be used in circumstances where a small bend angle is required.

Auxiliary plates may be attached to the same sleeve as a movable plate. FIGS. 10C, D shows the arrangement of FIGS. 10A, B in the state where the joint has been flexed. The slideable plate 14 has moved with respect to the plate slide member 16 so as to translate towards the hinge end. As shown, a small gap G is opened between the adjacent ends of the auxiliary plate 102 and the slideable plate 14, however, the parts may be dimensioned so that a gap does not form, or that a larger gap forms, depending on the application.

This apparatus may also be used to protect an elbow, other body part or other part of a prosthetic device. Such a device may include additional fixed or movable plates as required by the use. A space may be provided between the fixed and slideable plates for all or some of the flexure positions, or portions of fixed or slideable plates may be overlapped. The combination of a fixed and a slideable plate or two slideable plates may be disposed so as to provide continuous protection as the joint is flexed.

In another aspect the device may be sized and arranged to provide protection for other body parts where flexibility is desired, such as the torso. A combination of fixed, auxiliary and slideable plates, or multiple slideable plates, may be arranged to perform the same functions as for the bendable joints while minimizing the force needed to accommodate the body movements. In yet another aspect, another group of plates may be applied to the opposite side of a limb so as to protect the back side of a joint, as in body armor. In this aspect, more than one grouping of fixed, slideable and auxiliary plates may be associated with the sleeve.

Figure 11:
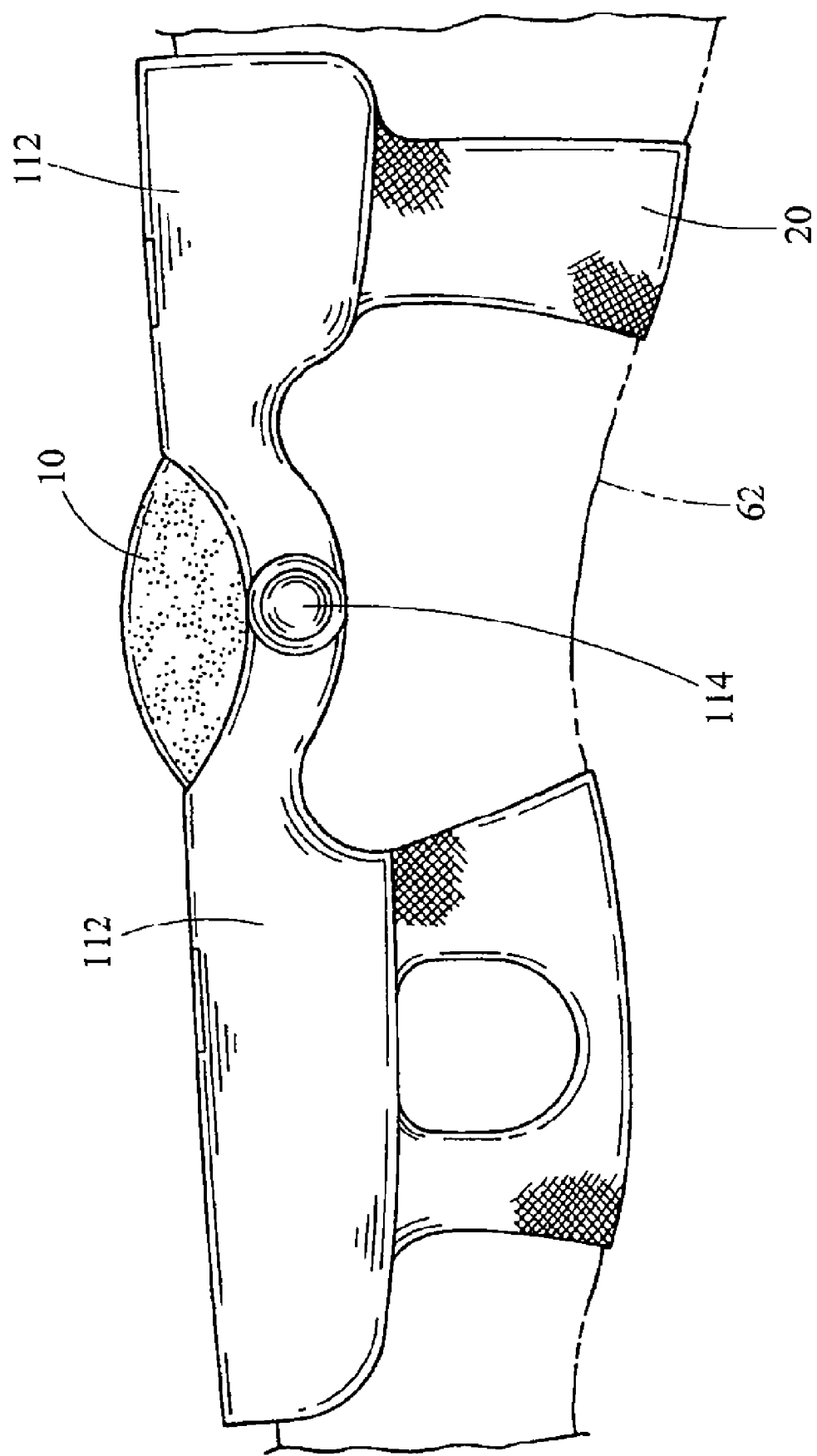
FIG. 11 illustrates a portion of an exoskeleton, where the plate slide member plate is journalled about an axis substantially corresponding to the fulcrum of the joint.

In a further example, the apparatus may be used to form an exoskeleton for a robotic device either acting autonomously or being used to aid in the motion or support of a limb, in whole or in part. FIG. 11 shows an assembly which may be used to support a limb 62. The general arrangement is similar to that in FIG. 2, and only significant differences are discussed where the view shown in FIG. 11 corresponds to FIG. 2E. Plate slide members 112 are fixedly attached to sleeve 10, and have extensions towards each other which overlap and are joined by a journal or pivot 114. The opposite side of the limb has a similar arrangement, such that an imaginary axis joining the journals 114 corresponds to the axis about which the joint is intended to flex. Slideable plates 14, as shown in FIG. 2F may be captivated by the plate slide members 112, and a fixed plate 12 disposed above the knee cap and between the adjacent ends of the slideable plates 14. In this example, the fixed plate 12 may be fixedly attached to the sleeve 10, or merely lie above the sleeve 10, being held in place by the slideable plates 14 and the hinges 22. The spring system 76, 78 may be replaced with hydraulic actuators which urge the translation of the slideable plate with respect to the plate slide assembly and thus transmit a force through the hinge 22 to the fixed plate 12. Although hydraulic actuators are described, the terminology is intended to encompass any linear actuator, which may be a linear motor or the like.

Figure 12A:
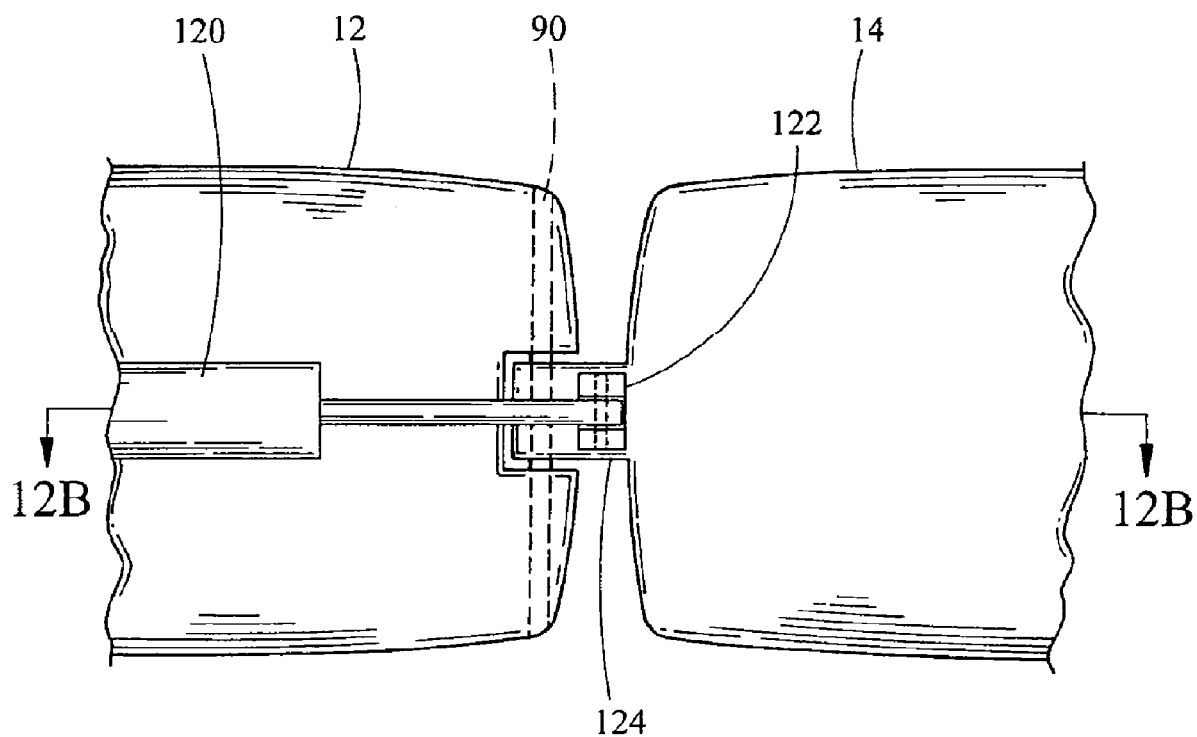
FIG. 12 illustrates the actuation of a hinge by hydraulic forcers.
Figure 12B:
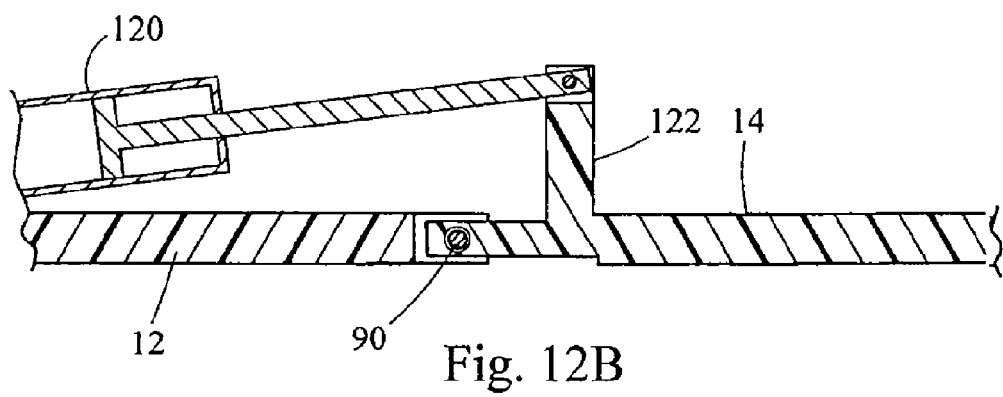

Additionally, the rotation of the hinge may be guided or assisted by a hydraulic actuator 120, acting in coordination with the hydraulic actuators used to urge the translation of the slideable plate. The hydraulic actuators 120 may be mounted to either the slideable plate 14 (as shown in FIG. 12), the slide plate 16 or an auxiliary plate. A lever arm 122 may be affixed to the hinge 124 so that the hydraulic actuators 120 may cause the hinge 124 to rotate about an axis 90. In another alternative, a stepper motor or other rotary actuator may be used in place of the hydraulic actuators 120, and the lever arm 122 may be omitted. The rotary actuator may be incorporated into the hinge.

In another aspect, where the exoskeleton is used in a robot, the slide plate members 112 may be fixedly attached to, or formed as part of, structural members having, for example, a function similar to long bones in a limb, and the slide plate members joined by a journal or pivot 114. The pivots 114 on either side of the joint may be joined by a solid axel (not shown). In such a circumstance, the fixed plate 12 may also be connected to the solid axel by a structure substantially perpendicular to the solid axel and the fixed plate 12.

The device has been described where the relative movement of the components is accomplished with minimal applied force. However, the device may also be designed to limit the extent of movement of a limb in order to prevent injury. For example, the plates and sleeves may be sized such that an interference fit between plates may occur when a limb is bent back beyond a straight position as would occur in a hyperextension situation. Interference fits between adjacent plates may also be used to assist in returning the sliding plates to an appropriate position after a joint has been straightened.

Distributing the external force through the sleeves may prevent or reduce the injury. The rotation of upper and lower limbs of a joint may similarly be restrained by the torsional properties of the hinge between the plates such that a limit is placed on the permitted relative rotation of adjacent plates, providing protection similar to the bending protection.

Although the descriptions and examples have mainly discussed the application to protection of humans, the plates and the connections therebetween and the methods of mounting the plates may be used equally in such situations as the adapting of prosthetic devices to have more human attributes, and to protect the mechanisms thereof, as well as to form the exoskeleton of a robotic device, in whole or in part. In such applications, fixed plates may be mounted directly to a support member in a permanent or non-permanent manner, with or without the use of a sleeve. Similarly, the slide member associated with a slideable plate may also be attached directly to a support member. Sleeves may be used as well and afford both cosmetic appeal and prevent the entry of dirt, dust or fluids into the mechanisms.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. An apparatus, comprising:
   a first plate, a second plate and a third plate, at least two of the first, the second or the third plate connected by a journal;
   a first slide plate and a second slide plate, slideably attachable to the first plate and the second plate, respectively;
   wherein the first slide plate and the second slide plate are each connectable to the third plate by a hinge or flexure located at a portion of each of the first and second slide plate proximal to the third plate.

2. The apparatus of claim 1, wherein at least the first and the second plates are attached to a flexible sleeve.

3. The device according to claim 1, where the flexible sleeve is comprised of a material which is conformable to a human body part.

4. The device according to claim 1, wherein the flexible sleeve is a plurality of sleeves.

5. The apparatus of claim 1, wherein the flexible sleeve is approximately a portion of a conical section.

6. The device according to claim 1, wherein the first plate and the second plate are sized and shaped to approximately conform to the shape of a human body part.

7. The device according to claim 1, wherein the second plate includes an engaging structure for slideably mating with a complimentary mating structure on the second slide plate.

8. The device of claim 1, wherein the first plate is attachable to a first structural member and the second plate is attachable to a second structural member.

9. The device of claim 1, wherein at least one of the first or the second slide plate is translatable with respect to a corresponding first plate or second plate by an actuator connected between at least one of the first slide plate or the second slide plate and one of the first plate, the second plate, or the third plate.

10. The device of claim 9, wherein the actuator is a hydraulic actuator.

11. The device of claim 9, wherein the actuator is a linear actuator.

12. The device of claim 11, wherein the linear actuator includes a motor.

13. A method of protecting or manipulating a body part, the method comprising:

providing a first, a second plate and a third plate, at least two of the first, the second or the third plates journally connected to each other;

providing a first slide plate and a second slide plate, each slide plate adapted to be slidably mounted to a corresponding first plate or second plate;

connecting at least one of the first slide plate or the second slide plate to the third plate with a hinge or flexure, wherein the a portion of the hinge or the flexure is attached to a portion of the corresponding first slide plate or second slide plate proximal to the third plate.

14. The method of claim 13, further comprising:

providing a linear actuator disposed between at least two of the first slide plate, the second slide plate, the first plate, the second plate, or the third plate, so as to permit the actuator to translate at the least the two plates with respect to each other.

* * * * *

UNITED STATES PATENT AND TRADEMARK OFFICE
CERTIFICATE OF CORRECTION

| | | |
|---|---|---|
| PATENT NO. | : 8,151,369 B2 | |
| APPLICATION NO. | : 13/053712 | |
| DATED | : April 10, 2012 | |
| INVENTOR(S) | : Keith D. Olson | |

It is certified that error appears in the above-identified patent and that said Letters Patent is hereby corrected as shown below:

In the Claims

In column 16, claim 13, line 5, after "adapted to be" replace "slidably" with --slideably--.

In column 16, claim 13, line 9, before "a portion of the hinge or the flexure" delete "the".

Signed and Sealed this
Second Day of October, 2012

David J. Kappos
*Director of the United States Patent and Trademark Office*